United States Patent [19]
Lawson et al.

[11] Patent Number: 5,968,911
[45] Date of Patent: *Oct. 19, 1999

[54] METHOD OF INDUCING VASORELAXATION TO TREAT PULMONARY HYPERTENSION

[75] Inventors: Charles A. Lawson, Verona, N.J.; David J. Pinsky, Riverdale, N.Y.; Arthur Smerling, New Rochelle, N.Y.; David M. Stern, Great Neck, N.Y.

[73] Assignee: The Trustees of Columbia University in the City of New York, New York, N.Y.

[ * ] Notice: This patent is subject to a terminal disclaimer.

[21] Appl. No.: 08/362,571

[22] PCT Filed: Oct. 4, 1994

[86] PCT No.: PCT/US94/11248

§ 371 Date: Feb. 18, 1997

§ 102(e) Date: Feb. 18, 1997

[87] PCT Pub. No.: WO95/09636

PCT Pub. Date: Apr. 13, 1995

Related U.S. Application Data

[63] Continuation-in-part of application No. 08/131,984, Oct. 4, 1993.

[51] Int. Cl.$^6$ ......................... C07H 19/167; C07H 19/20; A01N 43/90
[52] U.S. Cl. .............................. 514/46; 514/47; 514/261; 514/264; 514/740; 514/851
[58] Field of Search ................................. 514/46, 47, 261, 514/264, 740, 851

[56] References Cited

U.S. PATENT DOCUMENTS

| | | |
|---|---|---|
| 4,623,666 | 11/1986 | Kennedy . |
| 4,956,348 | 9/1990 | Gilbard . |
| 5,175,151 | 12/1992 | Afonso et al. . |
| 5,217,997 | 6/1993 | Levere et al. . |
| 5,250,700 | 10/1993 | Bagli et al. . |
| 5,362,747 | 11/1994 | Cowart et al. . |
| 5,366,977 | 11/1994 | Pollard et al. . |
| 5,370,989 | 12/1994 | Stern et al. . |
| 5,376,666 | 12/1994 | Duncia . |

OTHER PUBLICATIONS

A.G. Gilman, et al., "Goodman and Gilman's The Pharmacological Basis of Therapeutics", Published 1980 by Macmillan Publishing Co., Inc. (N.Y.)592–607 Archer, et al. *J. Appl. Physiol.* (1990) 68(2):735–747.

Brackett, et al., *Biochemical Pharmacology* (1990) 39(12):1897–1904.

Lawson, et al., abstract presented at American Heart Association Meeting, Atlanta, Georgia, Nov. 8–11, 1993; and Rossaint, et al. *The New England Journal of Medicine* (Feb. 11, 1993) 328(6):399–405.

*Primary Examiner*—Gary L. Kunz
*Attorney, Agent, or Firm*—John P. White; Cooper & Dunham LLP

[57] ABSTRACT

This invention provides a method of selectively decreasing pulmonary vascular resistance in a subject by administering endobronchially a drug chosen from among cAMP analogs, cGMP analogs, phosphodiesterase inhibitors, nitric oxide precursors, nitric oxide donors, and nitric oxide analogs.

47 Claims, 31 Drawing Sheets

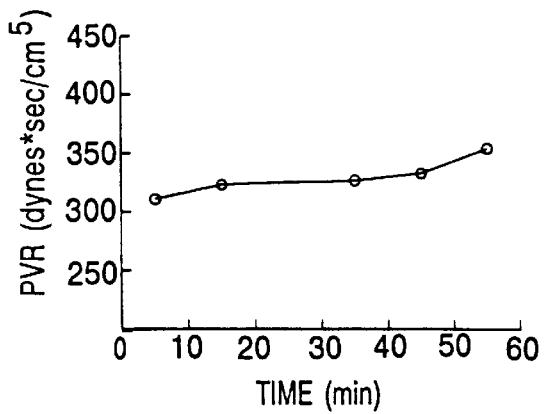
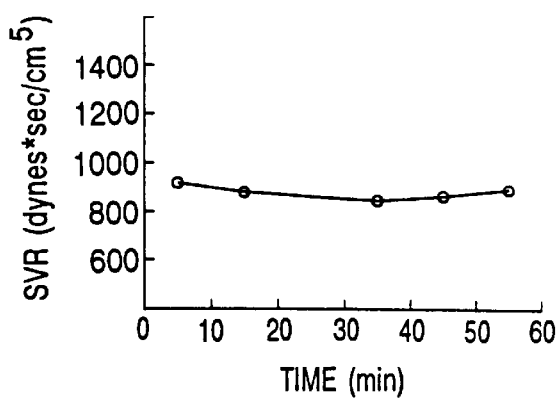
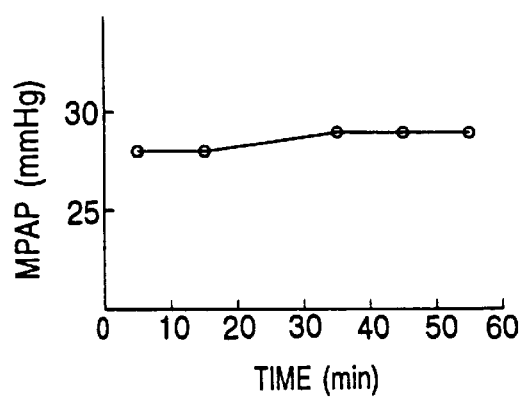
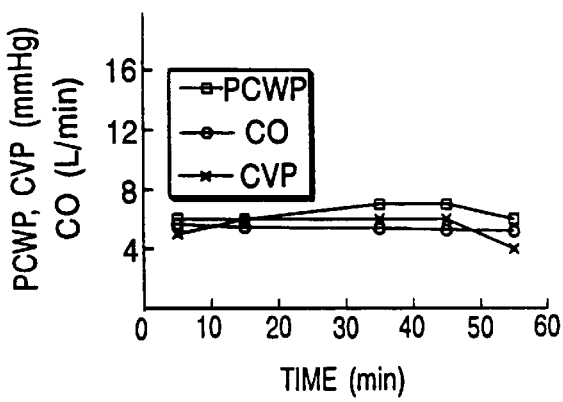
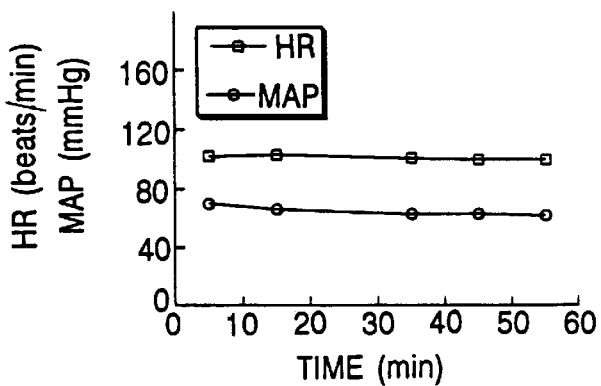

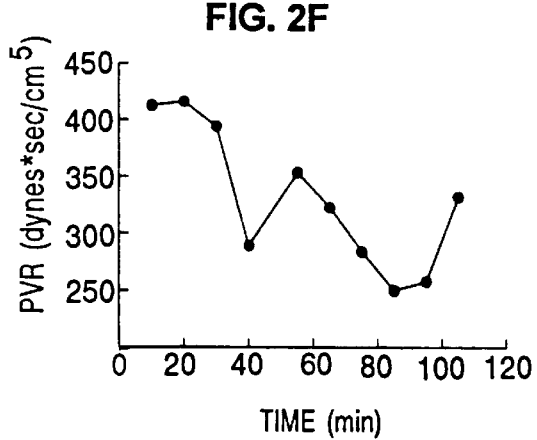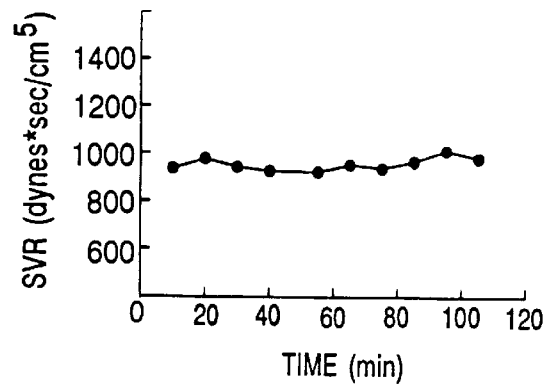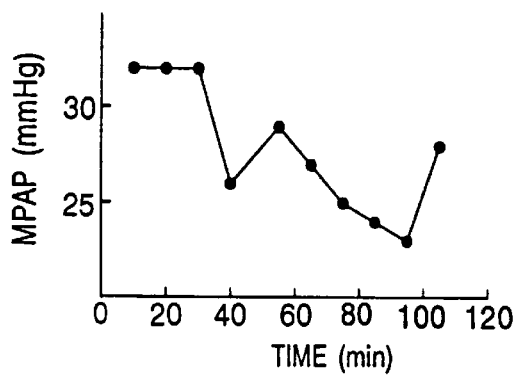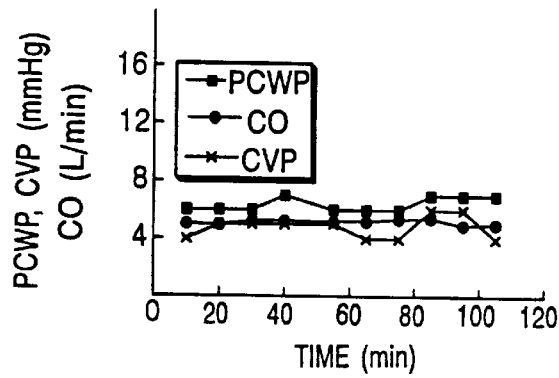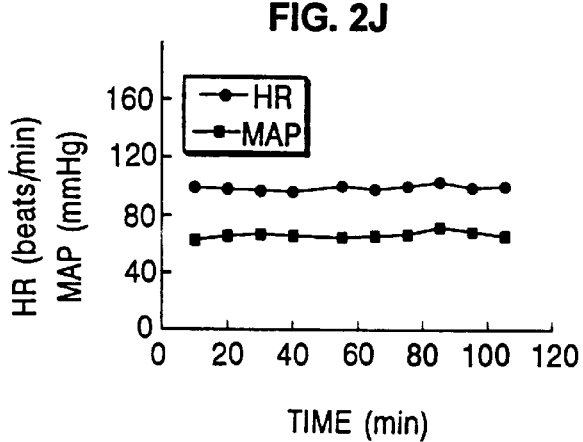

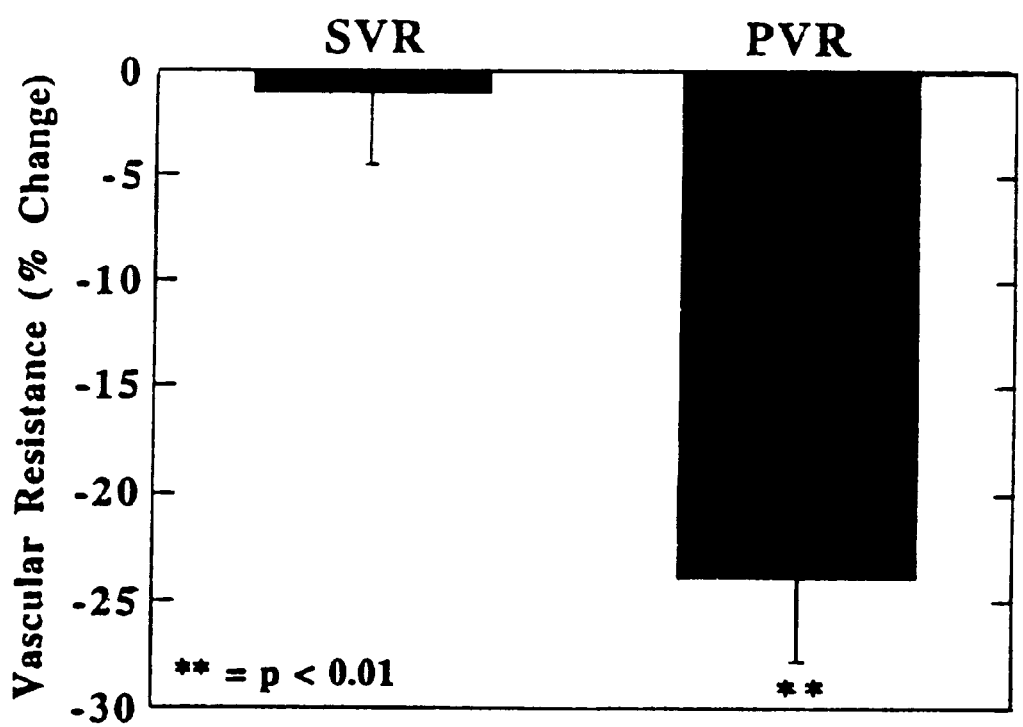

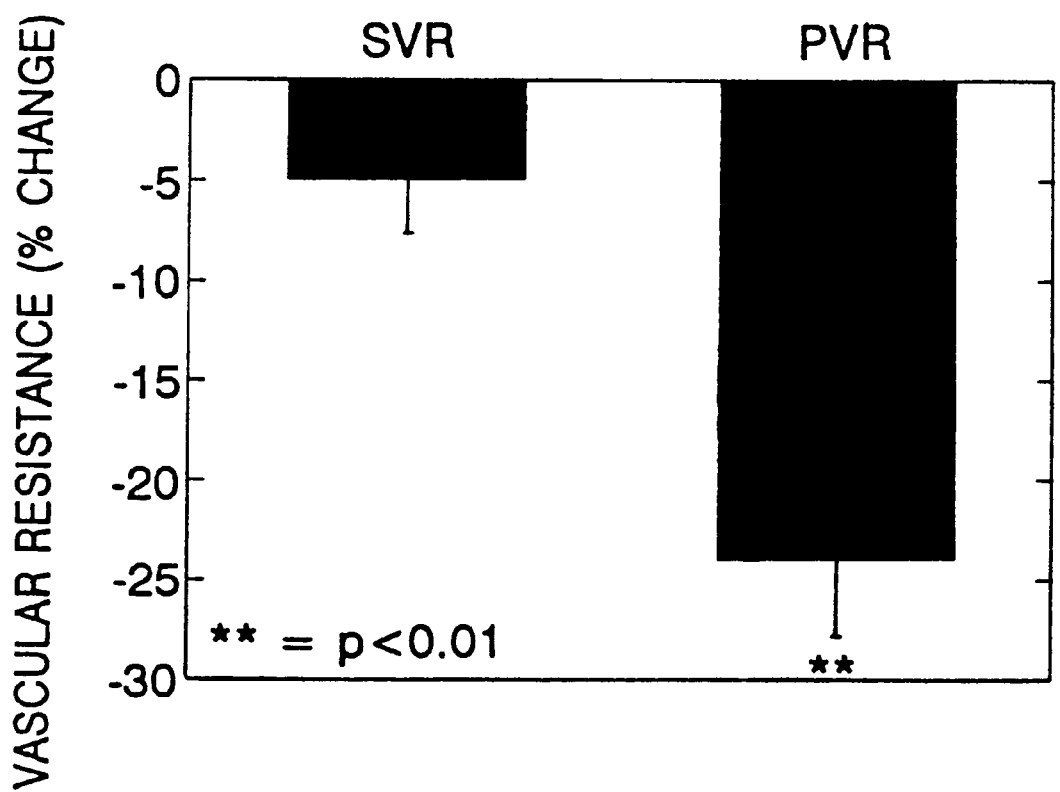

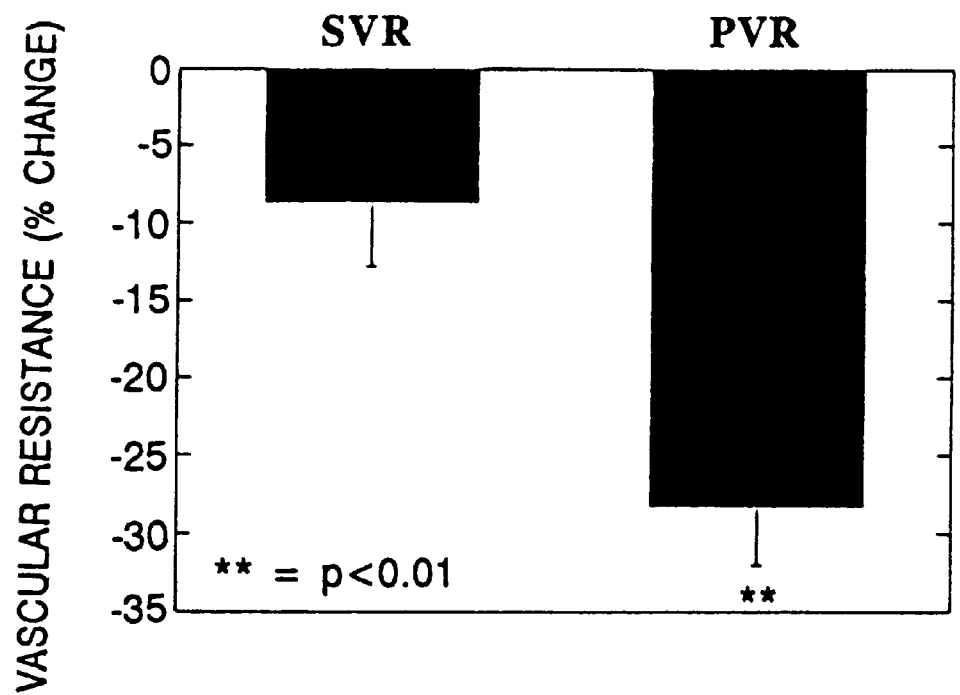

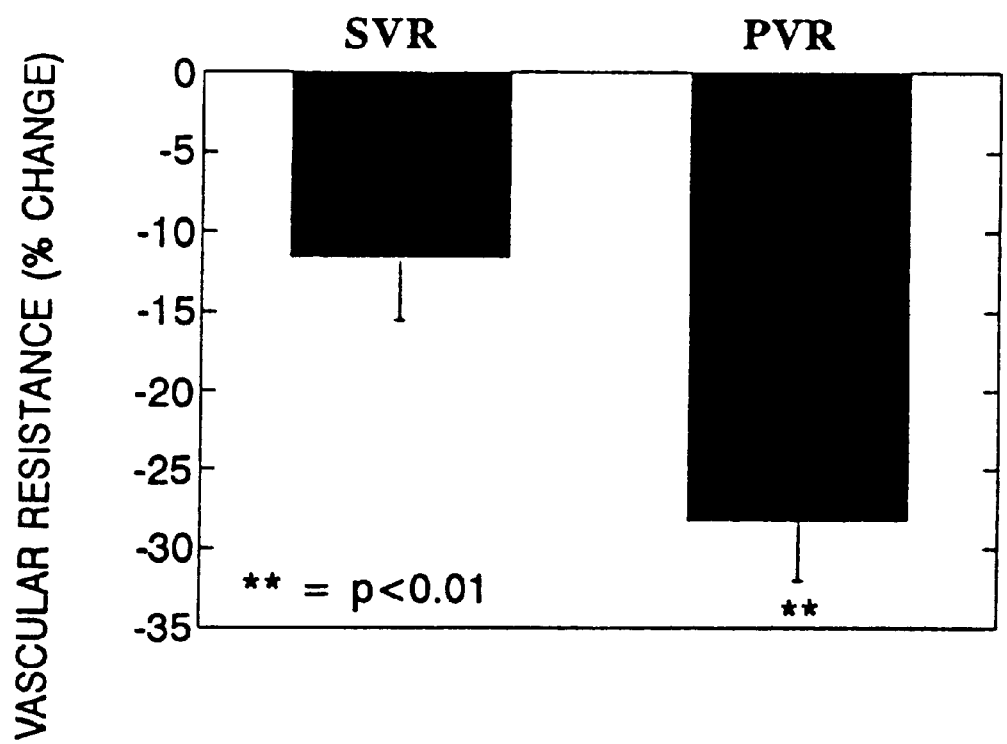

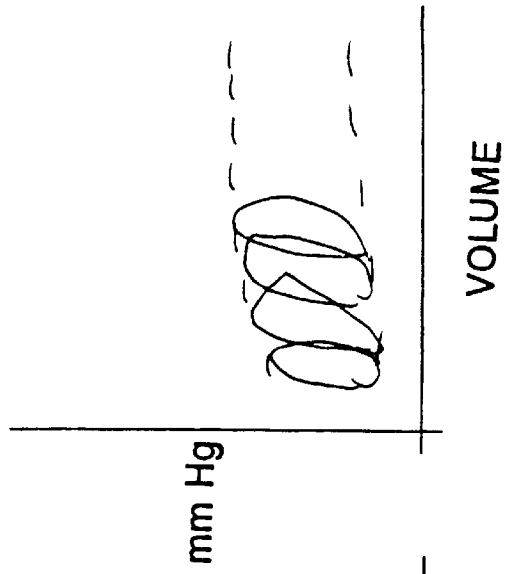
FIG. 8C POST ESMOLOL
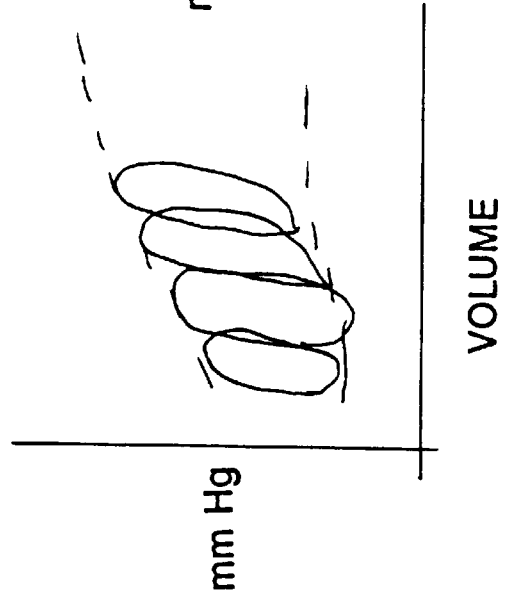
FIG. 8B POST 8-Br-cGMP
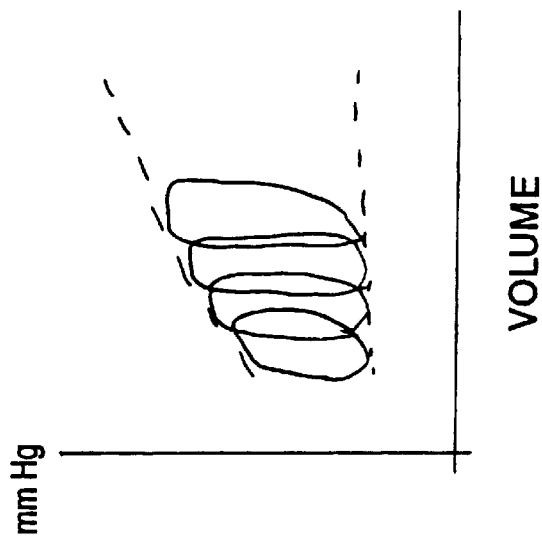
FIG. 8A BASELINE

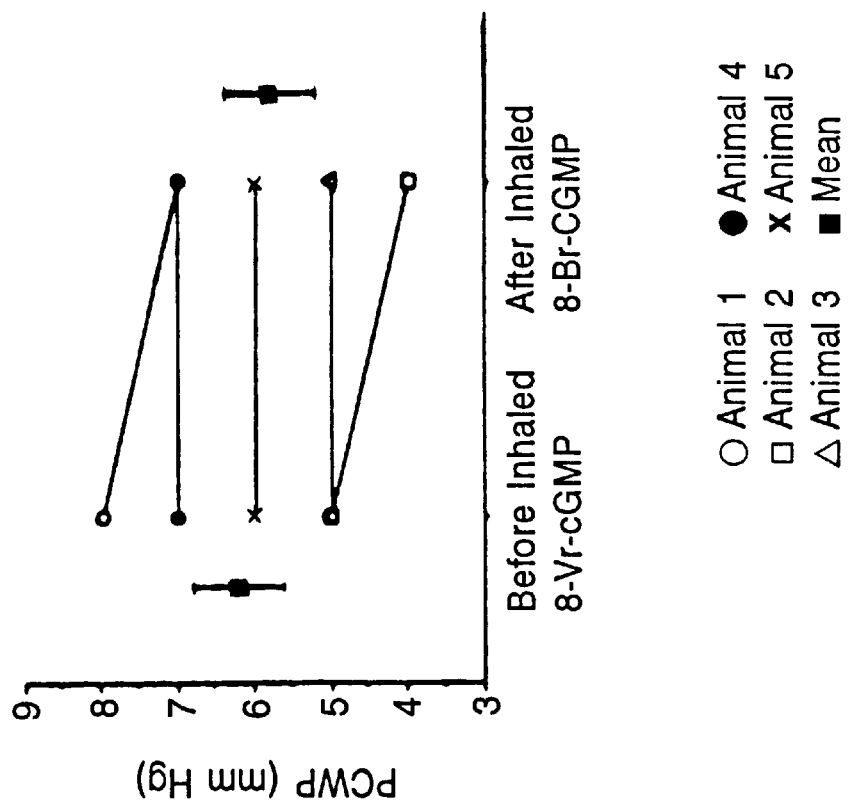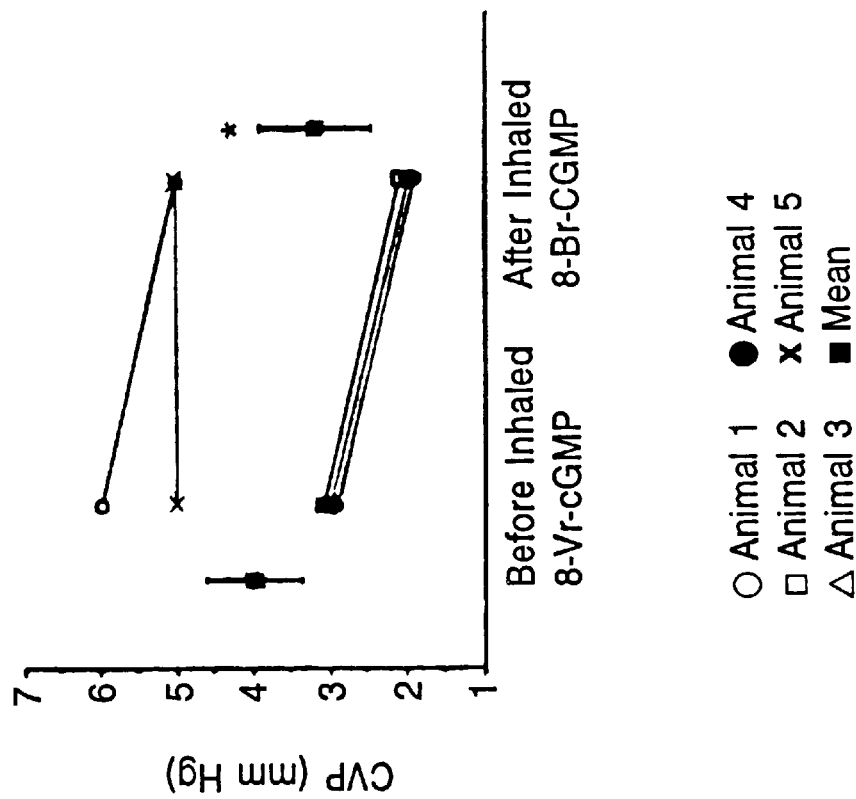

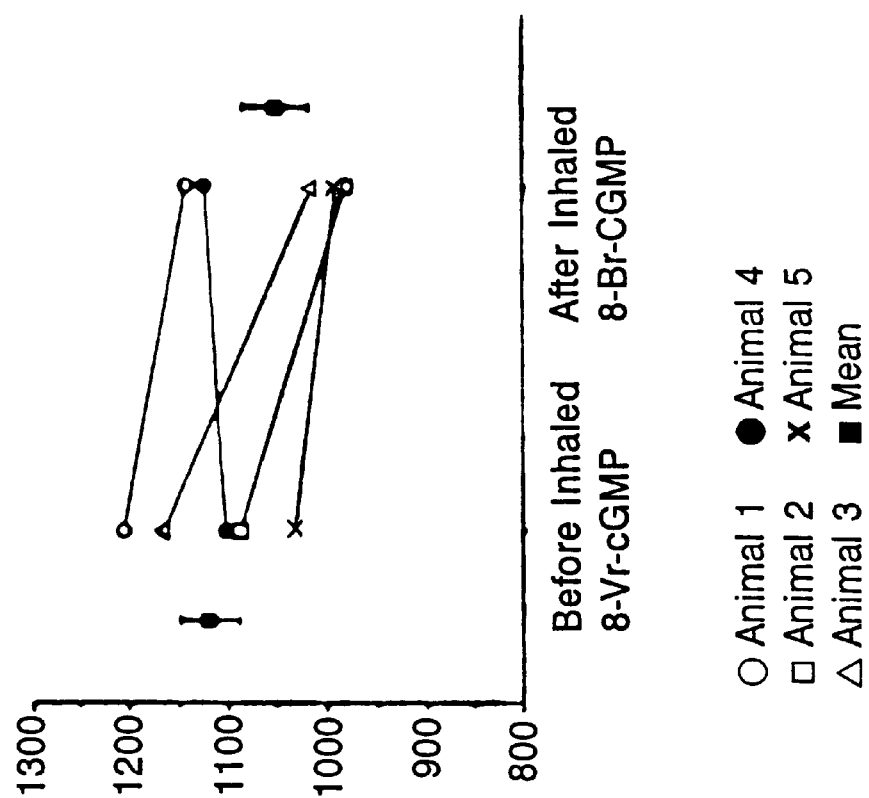
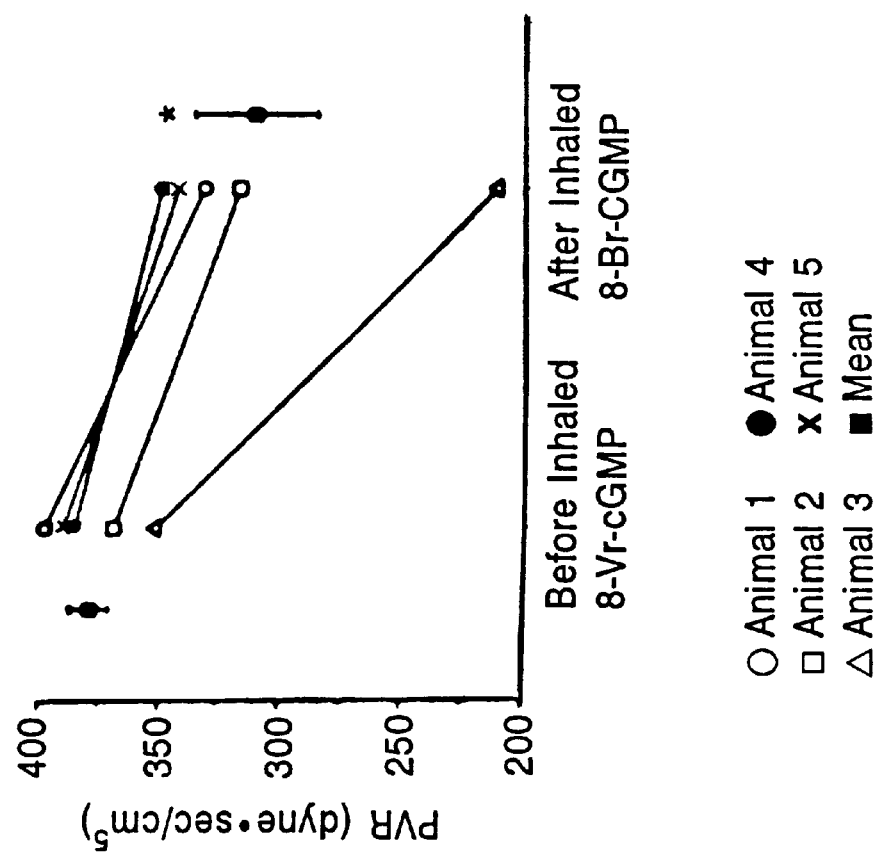

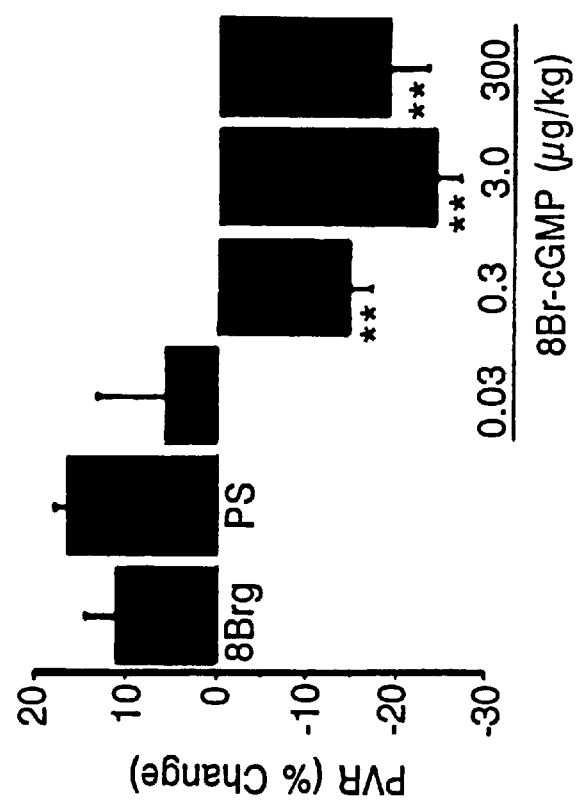
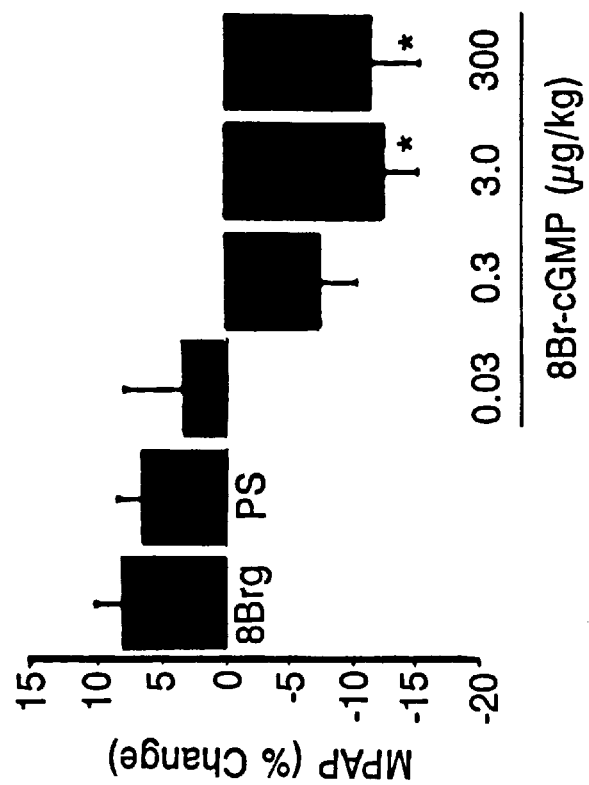
FIG. 16B
FIG. 16A

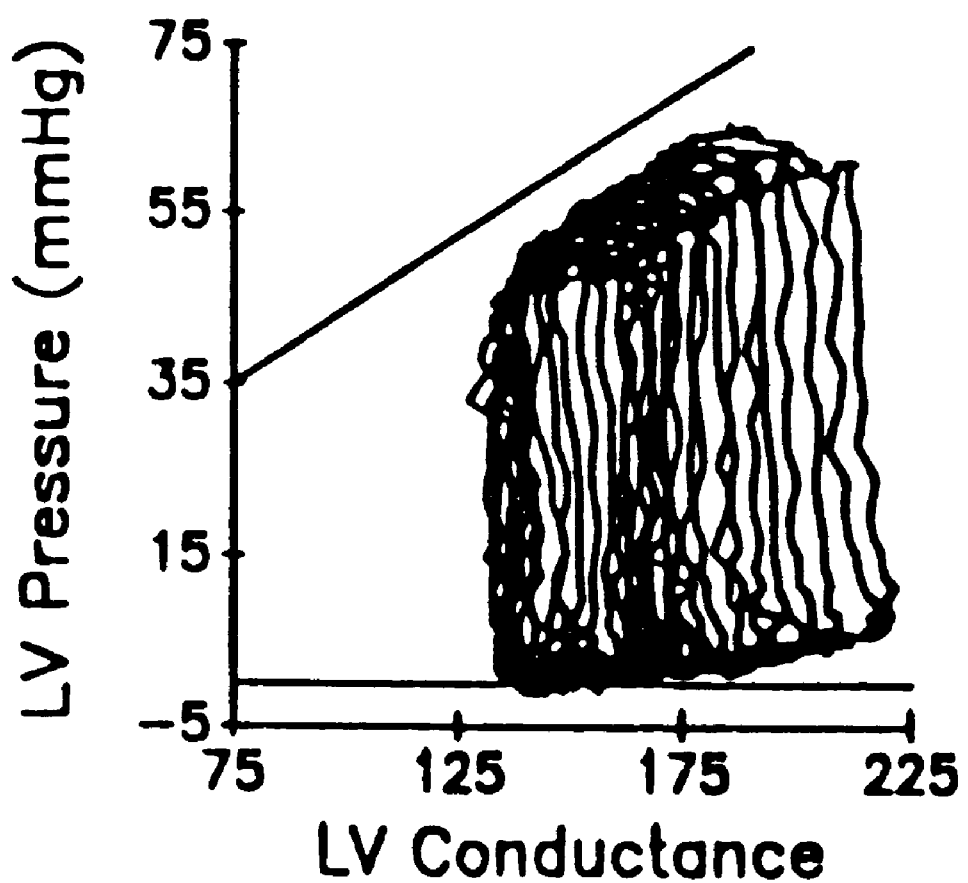

METHOD OF INDUCING VASORELAXATION TO TREAT PULMONARY HYPERTENSION

This is a 371 of PCT/US94/11248 filed Oct. 4, 1994, and a continuation-in-part of SN 08/131,984, filed Oct. 4, 1993.

The invention disclosed herein was made with Government support under NIH Grant Nos. 1 T3 GMO8464-01, HL42507, HL42833, and HL21006 from the Department of Health and Human Services. Accordingly, the U.S. Government has certain rights in this invention.

Throughout this application, various references are referred to within parentheses or by arabic numerals. Disclosures of these publications in their entireties are hereby incorporated by reference into this application to more fully describe the state of the art to which this invention pertains. Where not given in the text, full bibliographic citations for these references may be found at the end of each section, preceding the claims.

BACKGROUND OF THE INVENTION

Pulmonary hypertension is associated with significant morbidity and mortality, yet therapeutic options remain limited because agents which lower pulmonary vascular resistance (PVR) also lower systemic vascular resistance (SVR) (1). Nitric oxide (NO) gas has recently been shown to selectively lower PVR in pulmonary hypertension (2,3), but concerns remain involving its potential chromosomal effects (4), formation of toxic products from reaction with oxygen (4,5), logistic difficulties associated with delivery of a gas, and its short biological half-life, necessitating constant administration for continued effect (3,6).

Initial observations dealing with the use of cAMP and cGMP compounds go back to models of heart transplantation, where it was demonstrated that these systems were dysfunctional in the blood vessels of a transplanted heart. Supplementation of either the cGMP or the cAMP pathways could enhance the function of blood vessels within the graft, promoting successful transplantation. Stimulators of cAMP pathway used in these experiments included Sp-cAMPs, 8-Br-cAMP, db-cAMP, and phosphodiesterase inhibitors (indolidan, rolipram), all of which helped graft preservation. An antagonist of this pathway (RpcAMPS) blocked the beneficial effects of 8-Br-cAMP.

Nitric oxide is formed by cells lining blood vessels from the amino acid L-arginine, and leads to the formation of cGMP in the nearby cells. In the transplantation model, compounds which give off NO (nitroglycerin, nitroprusside), the NO precursor L-arginine, or 8-Br-cGMP (which acts like native cGMP but is capable of passing through cell membranes and therefore getting into cells) similarly benefitted heart preservation.

Both pathways (cAMP and cGMP) seemed to be dysfunctional in the setting of transplantation because of their roles in maintaining proper blood vessel function. Beneficial effects included improving blood flow, reducing damaging white blood cell infiltrations into blood vessels, preventing blood vessel leakiness, and preventing blood clot formation. The basis for these effects have been described in numerous basic science papers elsewhere, in which the roles of these compounds on these functions had been studied. Experiments performed in the context of lung transplantation indicated that these same beneficial effects were found in the blood vessels of the lungs.

SUMMARY OF THE INVENTION

This invention provides a method of decreasing pulmonary vascular resistance in a subject which comprises administering endotracheally or endobronchially an effective amount of a drug selected from the group consisting of cyclic nucleotides, phosphodiesterase inhibitors, nitric oxide precursors, nitric oxide donors, and nitric oxide analogs, thereby decreasing pulmonary vascular resistance.

This invention provides a method of selectively decreasing pulmonary vascular resistance in a subject which comprises administering endotracheally or endobronchially an effective amount of a drug selected from the group consisting of cyclic nucleotides, phosphodiesterase inhibitors, nitric oxide precursors, nitric oxide donors, and nitric oxide analogs, thereby decreasing pulmonary vascular resistance.

DESCRIPTION OF THE FIGURES

FIGS. 2A–2J: Simultaneous hemodynamic measurements from a representative animal following the establishment of pulmonary hypertension in the thromboxane analog model. (FIGS. 2A–2E) (A) Physiologic saline inhalation (5 ml). (FIGS. 2F–2J) (B) 8Br-cGMP inhalation (5 ml in physiologic saline, 3.3 μg/kg). Measurements include heart rate (HR, beats/min), central venous pressure (CVP, mm Hg), pulmonary artery wedge pressure (PCWP, mm Hg), mean arterial and mean pulmonary arterial pressures (MAP, MPAP, mm Hg), and thermodilution cardiac outputs (CO, L/min).

FIGS. 3A–3B: Effect of inhaled 8-Br-cGMP on systemic (SVR) and pulmonary (PVR) vascular resistance in the thromboxane analog model of pulmonary hypertension. 8Br-cGMP was administered endotracheally as a mist (2–614 μg/kg) delivered in a 5 ml volume of physiologic saline, and hemodynamics were measured as described. (A) The maximal decline in PVR and the simultaneous decrease in SVR are expressed as mean % change [100×(MAP OR MPAP post-8-Br-cGMP minus MAP or MPAP pre-8-Br-cGMP)/MAP or MPAP pre-8-Br-cGMP] ±SEM. (b) The maximal decrease in SVR is consistently less than the maximal decrease in PVR after inhalation of 8Br-cGMP. Values are as described in (A).

FIGS. 6A–6B: Effect of inhaled 8-Br-cGMP on pulmonary and systemic vascular resistance in the hypoxia-induced pulmonary hypertension. After baseline stabilization, pigs were ventilated with a hypoxic gas mixture as described in FIG. 1. (A) The maximal decline in PVR and the corresponding drop in SVR are expressed as in FIG. 2. (B) Maximal decline in PVR was compared with maximal decline in SVR as described for the thromboxane analog model in FIG. 2.

FIGS. 8A–8C: Effect of inhaled 8-Br-cGMP on load-independent measurement of ventricular function. Pressure volume loops were recorded with a conductance catheter placed in the left ventricle under fluoroscopic guidance, with intermittent caval occlusion performed to vary preload. Hypertonic saline was administered to standardize the conductance measurements (15), and esmolol (40 mg as an intravenous bolus) was given to demonstrate the effects of a known negative inotrope (data not shown). Systolic and diastolic function are described by the upper and lower tangents (respectively) to the pressure volume curve families, and are not different when compared before (A) or after (B) inhalation of 8-Br-cGMP (30 $\mu$g/kg) in 5 ml of normal saline delivered as a mist. Measurements were recorded for two hours (the 60 minute data is shown; there was no difference in ventricular function noted at any time point).

FIG. 15C: Effect of inhalationally administered 8-Br-cGMP (300 $\mu$g/kg) on hemodynamic parameters during the thromboxane analog infusion for each animal shown in Tables 1 and 2: Maximal and mean changes in CVP ($*=p<0.05$).

FIG. 15D: Effect of inhalationally administered 8-Br-cGMP (300 $\mu$g/kg) on hemodynamic parameters during the thromboxane analog infusion for each animal shown in Tables 1 and 2: Maximal and mean changes in PCWP.

FIG. 15G: Effect of inhalationally administered 8-Br-cGMP (300 $\mu$g/kg) on hemodynamic parameters during the thromboxane analog infusion for each animal shown in Tables 1 and 2: Maximal and mean changes in PVR ($*=p<0.05$).

FIG. 15H: Effect of inhalationally administered 8-Br-cGMP (300 $\mu$g/kg) on hemodynamic parameters during the thromboxane analog infusion for each animal shown in Tables 1 and 2: Maximal and mean changes in SVR.

FIG. 16A: Inhalation of different doses of 8-Br-cGMP (0.03 $\mu$g/kg, n=3; 0.3 $\mu$g/kg, n=3; 3.0 $\mu$g/kg, n=3; 300 $\mu$g/kg, n=5), 8-Bromoguanosine-5'monophosphate (8Brg, n=5), or physiologic saline (PS, n=5): Maximal changes in MPAP after 8Brg (300 $\mu$g/kg) dissolved in 5 mL PS, 5 mL PS as control, and different doses of 8-Br-cGMP as indicated, dissolved in 5 mL PS ($*=p<0.003$ vs. PS control).

FIG. 16B: Inhalation of different doses of 8-Br-cGMP (0.03 $\mu$g/kg, n=3; 0.3 $\mu$g/kg, n=3; 3.0 $\mu$g/kg, n=3; 300 $\mu$g/kg, n=5), 8-Bromoguanosine-5'monophosphate (8Brg, n=5), or physiologic saline (PS, n=5): Maximal changes in MAP.

FIG. 19C: Pressure volume loops within five minutes after intravenous esmolol (1 mg/kg). The end systolic pressure volume relationship demonstrates a negative inotropic effect.

DETAILED DESCRIPTION OF THE INVENTION

Figure 1A:
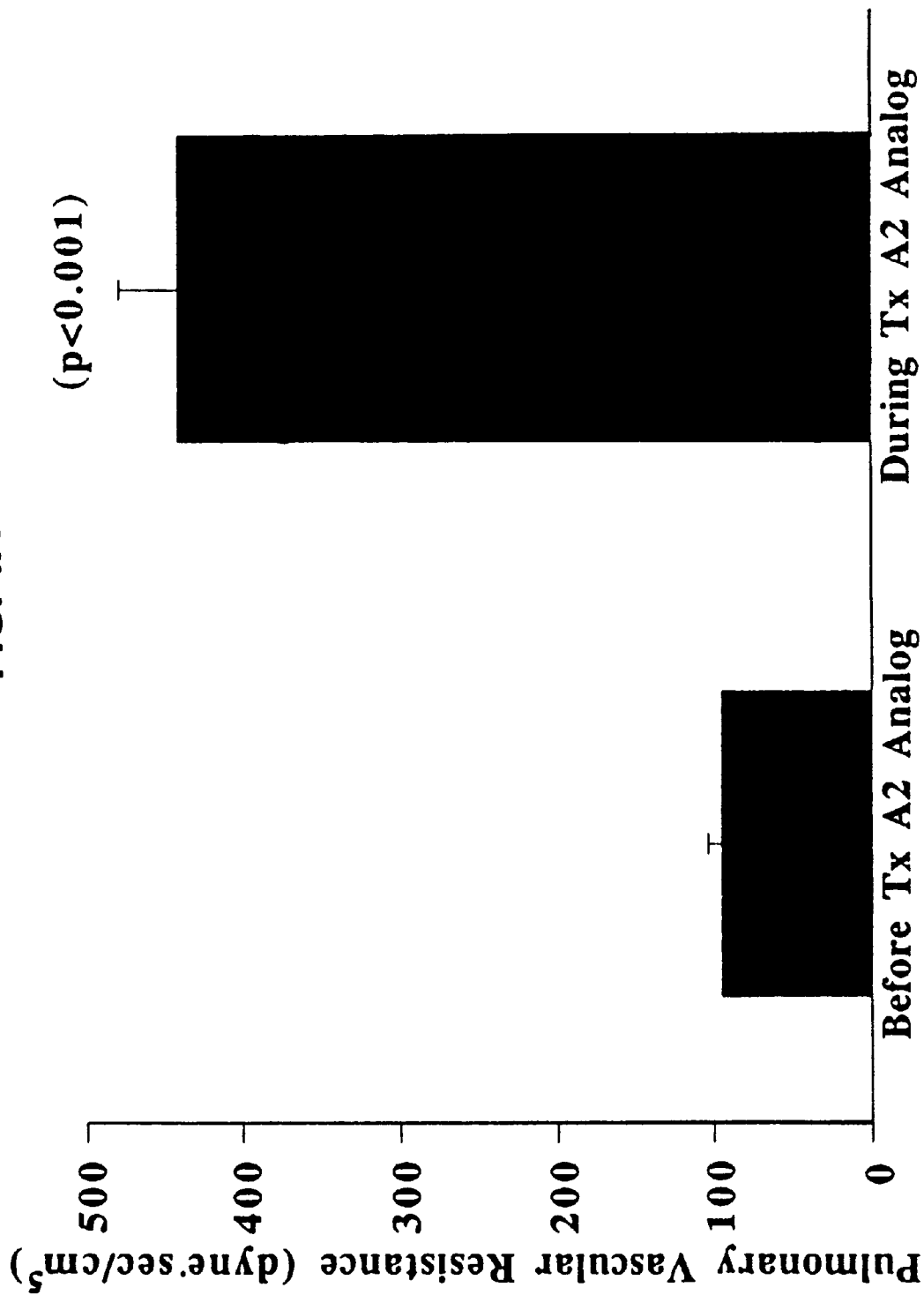
FIGS. 1A–1C: Establishment of pulmonary hypertension in three porcine models. (A) The thromboxane (Tx) $A_2$ analog 9,11-dideoxy-11α,9α-epoxymethanoprostaglandin $F_{2\alpha}$ was infused intravenously (n=9) initially at 0.1 μg/kg/min, and titered until a stable mean PA pressure of 30 mmHg was reached, after which no dosage adjustments were made. Bar graphs represent the mean±SEM of the baseline measurements of pulmonary vascular resistance (PVR) versus those obtained 1 hour after a stable dose of Tx was achieved (range 0.07–0.11 μg/kg/min). (B) Hypoxic pulmonary artery vasoconstriction was induced (n=8) by ventilation with a gas mixture consisting of nitrogen and oxygen mixed so that inhaled $O_2$ was 9–10%. Bar graphs represent the mean±SEM of the baseline measurements of PVR versus those obtained after hypoxic ventilation. (C) ARDS model of pulmonary hypertension was created by infusing oleic acid (0.3 ml/kg, n=6) over 1–2 hours, followed by measuring PVR±SEM after stable measurements were recorded during a one hour period.

This invention provides a method of decreasing pulmonary vascular resistance in a subject which comprises administering endotracheally or endobronchially an effective amount of a drug selected from the group consisting of cyclic nucleotides, phosphodiesterase inhibitors, nitric oxide precursors, nitric oxide donors, and nitric oxide analogs, thereby decreasing pulmonary vascular resistance. Administering endotracheally means administering via the trachea. Administering endobronchially means administering via a bronchus or bronchi. As used herein bronchus refers to one of the primary divisions of the trachea or to one of the further divisions which connect the primary bronchi and the bronchioles.

In a specific embodiment of this method, pulmonary vascular resistance is decreased by at least about twenty-four percent. In another embodiment, the pulmonary vascular resistance is decreased by up to about thirty-four percent. In a preferred embodiment, PVR is decreased by up to about sixty-four percent. In another embodiment, the pulmonary vascular resistance is decreased between about twenty-four percent and about thirty-four percent. In another embodiment, the pulmonary vascular resistance is decreased between about twenty-four percent and about sixty-four percent.

In a preferred embodiment, the pulmonary vascular resistance is decreased for over ninety minutes. In a specific embodiment maximal decrease in pulmonary vascular resistance occurs at about seventy minutes after administering the drug.

This invention also provides for a method of selectively decreasing pulmonary vascular resistance in a subject which comprises administering endotracheally or endobronchially an effective amount of a drug selected from the group consisting of cyclic nucleotides, phosphodiesterase inhibitors, nitric oxide precursors, nitric oxide donors, and nitric oxide analogs, thereby decreasing pulmonary vascular resistance. Selectively decreasing pulmonary vascular resistance means decreasing pulmonary vascular resistance by a greater degree than systemic vascular resistance is decreased. In a specific embodiment, the ratio of the percent change in systemic vascular resistance to the percent change in the pulmonary vascular resistance (ΔSVR/ΔPVR) is about 0.5 or less. In a more specific embodiment, the ratio of the percent change in systemic vascular resistance to the percent change in the pulmonary vascular resistance (ΔSVR/ΔPVR) is about 0.3 or less. In a preferred embodiment, the ratio of the percent change in systemic vascular resistance to the percent change in the pulmonary vascular resistance (ΔSVR/ΔPVR) is about 0.04 or less.

This invention also provides for a method of selectively counteracting the effects of a vasoconstrictor which comprises administering endotracheally or endobronchially an effective amount of a drug selected from the group consisting of cyclic nucleotides, phosphodiesterase inhibitors, nitric oxide precursors, nitric oxide donors, and nitric oxide analogs, thereby decreasing pulmonary vascular resistance. The vasoconstrictor may be a product of the subject's own body or it may be a vasoconstrictor that is administered to the subject. The drug may be administered before, during, or after the vasoconstrictor is administered. In a specific embodiment, the vasoconstrictor is thromboxane $A_2$. In another specific embodiment the vasoconstrictor is thromboxane $A_2$ analog U-46619.

This invention provides for a method of treating pulmonary hypertension in a subject which comprises administering endotracheally or endobronchially an effective amount of a drug selected from the group consisting of cyclic nucleotides, phosphodiesterase inhibitors, nitric oxide precursors, nitric oxide donors, and nitric oxide analogs, thereby decreasing pulmonary vascular resistance.

This invention also provides for a method of treating a pulmonary condition in a subject which comprises administering endotracheally or endobronchially an effective amount of a drug selected from the group consisting of cyclic nucleotides, phosphodiesterase inhibitors, nitric oxide precursors, nitric oxide donors, and nitric oxide analogs, thereby decreasing pulmonary vascular resistance. In an embodiment of this method the pulmonary condition is selected from the group consisting of primary pulmonary hypertension, chronic obstructive pulmonary disease, adult respiratory distress syndrome, congenital heart disease, asthma, cystic fibrosis, sarcoidosis, cor pulmonale, pulmonary embolism, bronchiectasis, emphysema, Pickwickian syndrome, sleep apnea, congestive heart failure, and valvular heart disease.

In the method of decreasing pulmonary vascular resistance in a subject, the subject may be any animal with lungs or lung-like structures. In a specific embodiment, the subject is a mammal. In a more specific embodiment, the mammal is a pig. In another specific embodiment, the mammal is a human.

In an embodiment, the administering comprises injecting a liquid containing the drug via the trachea or a bronchus.

In another embodiment the administering comprises inhaling the drug in an aerosol form. In a specific embodiment the aerosol particle size is between about 0.5 micrometers and about 10 micrometers.

In a specific embodiment the aerosol is generated by a nebulizer.

In one embodiment the aerosolized drug is administered as an aqueous solution. Preferably, the aerosolized drug is administered as a lipid soluble aqueous solution. In another embodiment the aerosolized drug is administered as a micronized powder.

This invention also provides a method of decreasing pulmonary vascular resistance in a subject which comprises administering endotracheally or endobronchially an effective amount of a cyclic nucleotide, thereby decreasing pulmonary vascular resistance.

In an embodiment the cyclic nucleotide is membrane permeant. In another embodiment the cyclic nucleotide is an agonist of protein kinase A. In another embodiment the cyclic nucleotide is an agonist of protein kinase G. In another embodiment the cyclic nucleotide increases cellular cAMP. In another embodiment the cyclic nucleotide increases cellular cGMP. In another embodiment the cyclic nucleotide is resistant to degradation by an enzyme. In a specific embodiment, the cyclic nucleotide is resistant to degradation by phosphodiesterase.

In an embodiment the cyclic nucleotide is a cGMP analog. In a specific embodiment the cGMP analog is 8-bromo-3', 5'-cyclic guanosine monophosphate. In another embodiment the cGMP analog is 8-PCPT-cGMP. In another embodiment the cGMP analogue is Sp-8-Br-cGMPS.

In an embodiment the cyclic nucleotide is a cAMP analog. In a specific embodiment the CAMP analog is dibutyryl-3', 5'-cyclic adenosine monophosphate. In another embodiment the cAMP analog is 8-bromo-3',5'-cyclic adenosine monophosphate. In another embodiment the cAMP analog is Sp-cAMPS.

In an embodiment the effective amount of the drug is at least about 0.03 micrograms per kilogram of body weight. In a more specific embodiment the effective amount of the drug is between about 2 micrograms per kilogram of body weight to about 20 micrograms per kilogram of body weight.

In an embodiment the effective amount of 8-bromo-3',5'-cyclic guanosine monophosphate is at least about 0.03 micrograms per kilogram of body weight. In a preferred embodiment the effective amount of 8-bromo-3',5'-cyclic guanosine monophosphate is between about 2 micrograms per kilogram of body weight to about 20 micrograms per kilogram of body weight.

This invention also provides for the method of decreasing pulmonary vascular resistance further comprising administering a permeabilizing solvent. A permeabilizing solvent is a solvent which facilitates the passage of the drug through the cell membrane of the cells of the trachea or bronchus, particularly when the drug is a cyclic nucleotide. In a preferred embodiment the permeabilizing solvent is dimethylsulfoxide.

This invention also provides a method of decreasing pulmonary vascular resistance in a subject which comprises administering endotracheally or endobronchially an effective amount of a phosphodiesterase inhibitor, thereby decreasing pulmonary vascular resistance. In a specific embodiment the phosphodiesterase inhibitor is selected from the group consisting of isobutylmethylxanthine, indolidan, rolipram, 2-o-propoxyphenyl-8-azapurin-6-one (M&B 22948; Zaprinast), trequensin, amrinone, and milrinone. In a more specific embodiment the phosphodiesterase inhibitor is isobutylmethylxanthine. In another specific embodiment the phosphodiesterase inhibitor is 2-o-propoxyphenyl-8-azapurin-6-one (M&B 22948).

Phosphodiesterase (PDE) inhibitors are commonly categorized according to five families (See, W. J. Thompson, Pharmac. Ther. (1991) 51: 13–33; and J. P. Hall, Br. J. clin. Pharmac. (1993) 35: 1–7) (However, this classification is not universal and other classification schemes can be found in the literature.): PDE I - $Ca^{+2}$/Calmodulin-activatable; PDE II - cGMP activatable; PDE III - cGMP inhibitable; PDE IV - cAMP-specific; PDE V - cGMP-specific. These families include, but are not limited to, the following phosphodiesterase inhibitors:

Family I - calmodulin antagonists (e.g., phenothiazines, W-7, CGS 9343B), vinpocetine (TCV-3B), HA-558, 8-methoxymethyl-3-isobutyl-1-methylxanthine, KW-6 (isoquinoline derivative, 8-methylamino-3-isobutyl-1-methylxantine (MIMAX), and dibenzoquinazoline diones (Dihydroisoquinoline derivative.

Family II - Trequinsin (HL 725).

Family III - Indolidan (LY 195115), Cilostamide (OPC 3689), Lixazinone (RS 82856), Y-590, Imazodan (CI 914), SKF 94120, Quazinone, IC 153, 110, Cilostazol (OPC 13013), Bemorandan (RWJ 22867), Siguazodan (SK&F 94836), Adibendan (BM 14,478), Milrinone (WIN 47203), Enoximone (MDL 17043), Pimobendan (UD-CG 115, MCI-154), Saterinone (BDF 8634), and Sulmazole (ARL 115).

Family IV - Rolipram (ZK 62711; Pyrrolidone), RO 20–1724 (Imidazolidinone), SQ 64442 (Etazolate), and Denbufylline (BRL 30892).

Family V - Zaprinast (M&B 22948), and Dipyridamole (DSCG).

This invention also provides a method of decreasing pulmonary vascular resistance in a subject which comprises administering endotracheally or endobronchially an effective amount of drug selected from the group consisting of nitric oxide precursors, nitric oxide donors, and nitric oxide analogs, thereby decreasing pulmonary vascular resistance.

In a specific embodiment, the nitric oxide precursor is L-arginine. In a specific embodiment the nitric oxide donor is selected from the group consisting of diethylamine NONOate and spermine NONOate. In an embodiment, the nitric oxide analog is selected from the group consisting of nitroglycerin, nitroprusside, Sin-1, and SNAP. In an embodiment, the nitric oxide donor is selected from the group consisting of nitroglycerin, nitroprusside, Sin-1, and SNAP.

This invention will be better understood from the Experimental Details which follow. However, one skilled in the art will readily appreciate that the specific methods and results discussed are merely illustrative of the invention as described more fully in the claims which follow thereafter.

Experimental Details

First Series of Experiments

There are currently no effective therapies for pulmonary hypertension. Although the gas nitric oxide (NO) selectively dilates the pulmonary vascular bed, it is difficult to administer, has a short biologic half-life, and is potentially toxic. It was hypothesized that stimulation of the nitric oxide pathway using a nonhydrolyzable, membrane permeant analog of cGMP such as 8-Br-cGMP (7,8,9) or Sp-8-Br-cGMPS, or the cAMP analogs dibutyryl cAMP or 8-Br-cAMP which are administered via inhalation would confer relative pulmonary selectivity and circumvent the difficulties associated with administration of NO. These studies using three porcine models of pulmonary hypertension demonstrate the potential therapeutic usefulness of administering cGMP/cAMP analogs for the treatment of pulmonary vasoconstrictive disorders. Pulmonary hypertension was induced in 23 pigs by an intravenous thromboxane $A_2$ analog, U-46619, (Tx, n=9), hypoxic ventilation (H, n=8), or oleic acid (OA, n=6). Because NO increases cyclic guanosine 3'-5'-monophosphate (cGMP) levels in vascular smooth muscle, tests were done to determine whether inhalation of a membrane permeable cGMP analog to cause the highest possible pulmonary concentrations could cause selective pulmonary vasodilation in several models of pulmonary hypertension. In a comparison of aerosolized intratracheal inhalation of 8Br-cGMP with physiologic saline, pulmonary vascular resistance (PVR) declined by 24±3.8% ($p<0.001$), 28±3.7% ($p<0.01$), and 34±8.1% ($p<0.05$), for the Tx, H, and OA models, respectively. This compares favorably with PVR reduction seen following inhaled NO (50 ppm) (ΔPVR for 8-Br-cGMP was 50% of the ΔPVR for NO in the Tx model). The declines in systemic vascular resistance (SVR) following intratracheal 8Br-cGMP (1±4% and 9±4%, respectively) was significantly less (P<0.01) than the declines in PVR in the Tx and H models, but were similar in the OA model. Intravenous 8Br cGMP lowers PVR and SVR to a similar degree. 8Br-cGMP lowers PVR in a time and dose-dependent manner, with maximal effect achieved after one hour at doses as low as 0.03 μg/kg. The selective decline in PVR was not mimicked by inhalation of guanosine-5'monophosphate, suggesting that stimulation of the NO/cGMP pathway beyond the level of NO results in selective pulmonary vasodilation independent of stimulation of purine receptors. Pressure-volume loops constructed at different preloads using an intraventricular conductance catheter demonstrate little effect of inhaled 8Br-cGMP on ventricular contractility, suggesting that this agent may be given safely in the setting of cor pulmonale. These studies demonstrate that inhalation of an agent which is an analog of cGMP can selectively reduce PVR, and may be useful in pulmonary vasoconstrictive diseases.

EXPERIMENTAL METHODS

This experimental protocol was approved by the Columbia University Institutional Animal Care and Use Committee. Female swine (Hampshire or Yorkshire breeds, 35–70 kg) were premedicated, intubated, anesthetized and given a continuous infusion of muscle relaxant. The electrocardiogram was monitored (Datascope 2000, Datascope, Paramus, N.J.). Ventilation was controlled with an Ohmeda 7000 anesthesia ventilator (Ohmeda, Madison, Wis.) attached to an Ohmeda VMC anesthesia machine (BOC, W. Yorkshire, UK). Respiratory gases and airway pressures were monitored with an Ohmeda RGM 5250 analyzer (Ohmeda, Louisville, Colo.). An arterial catheter was inserted percutaneously into the femoral artery and the right external jugular vein was exposed via cutdown. An 8.5 F introducer sheath (Arrow, Reading, Pa.) was inserted into the external jugular vein, followed by placement of a 7.5 F pulmonary artery thermodilution catheter (Baxter Edwards Critical Care, Irvine, Calif.) which was advanced to the pulmonary artery with hemodynamic monitoring. Arterial, pulmonary artery, central venous, and pulmonary capillary sedge pressures were transduced (Abbott, North Chicago, Ill.) at right atrial level, and displayed on Datascope 2000 monitors (Paramus, N.J.). Animal temperature was measured continuously by rectal probe and maintained by infrared heating lamps. A cardiac output computer (Edwards Critical Care, Irvine, Calif.) using the thermodilution technique was used to measure cardiac output. Blood gas measurements for pH, $CO_2$ and $O_2$ content (mm Hg), and hemoglobin oxygen saturation were performed on a calibrated arterial blood gas analyzer (Nova Biomedical, Waltham, Mass.).

Hemodynamics were recorded at end expiration at baseline and every 10–15 minutes thereafter, and included measurements of heart rate (HR, beats/min), central venous pressure (CVP, mm Hg), pulmonary artery wedge pressure (PCWP, mm Hg), mean arterial and mean pulmonary arterial pressures (MAP, MPAP, mm Hg), and thermodilution cardiac outputs (CO, L/min). Three repetitive measurements of cardiac output using iced saline injection were averaged for each time point. When a stable baseline PVR was demonstrated, pulmonary hypertension was induced by 1) continuous intravenous infusion of the thromboxane $A_2$ analog (9,11-dideoxy-11α,9α-epoxymethanoprostaglandin $F_{2α}$ (10) (Sigma Chemical Co., St. Louis, Mo.) at a rate which resulted in a mean PA pressure of ≈30 mm Hg (0.07–0.11 μg/kg/min); 2) ventilation with a hypoxic gas mixture containing oxygen and nitrogen with the proportion of oxygen titrated to a mean PA pressure ≈30 mm Hg, with continuous hypoxia monitored by inhaled (≈10%) and arterial ($paO_2$) ≈35 mm Hg) oxygenation; 3) intravenous infusion of oleic acid (Sigma) 0.3 ml/kg over 1 hour. After stable measurements of PVR in the hypertensive state were achieved, aerosolized physiologic saline (0.9% sodium chloride) was given endotracheally, followed by at least one hour of observation. After observing consistent measurements of PVR, 8Br-cGMP (Sigma) was then given endotracheally (0.03–614 μg/kg in a 5 ml volume of physiologic saline, administered over 5 minutes) and hemodynamic data were recorded every 10–15 minutes. The normal saline and test compounds dissolved in normal saline were delivered endotracheally as a mist. Intravenous administration consisted of dissolving 300 μg/kg 8Br-cGMP in 5 ml of physiologic saline and injecting the solution as a bolus. In other experiments, 8-bromoguanosine-5'monophosphate (272 μg/kg, Sigma), Sp-cGMPS (Biolog, La Jolla, Calif.), dibutyryl cAMP (db-cAMP) or 8-Br-cAMP were similarly administered. NO (Airco, Lodi, N.J.) at a concentration of 50 ppm was administered during controlled ventilation after repeated measurements indicated unchanging pulmonary hypertension. At least 10 minutes of continuous NO inhalation elapsed before hemodynamic measurements were taken.

Measurement of Ventricular Function: Previous reports have suggested that NO and 8-Br-cGMP may exert some direct negative inotropic actions (11–14). In order to assess whether 8Br-cGMP has any such effects, experiments were performed in 2 animals in which pulmonary hypertension was not induced. LV contractile state was assessed in these animals by measuring the end-systolic pressure-volume relations (ESPVR). A 7F conductance catheter (10 pole, Webster Labs Inc., Baldwin Park, Calif.) was introduced into the carotid artery and the tip positioned in the left ventricular apex under fluoroscopic guidance. The abdominal inferior vena cava was exposed and venous return was impeded as needed with a snare. Conductance measurements were calibrated by estimating parallel conductance with a 10 ml bolus of hypertonic saline (5%) as described previously (15,16). LV pressure was measured using a Statham strain gauge connected to the end lumen in the conductance catheter. Data were digitized 200 Hz sampling rate) on a PC compatible computer and analyzed off-line with custom designed software. Pressure-volume loops were obtained at different preloads during brief periods of IVC occlusion, and end-systolic pressure ($P_{es}$) and volumes ($V_{es}$) were identified in the standard fashion. The slope ($F_{es}$) and volume axis intercept ($V_o$) were calculated using linear regression analysis of $V_{es}$ against $P_{es}$: $P_{es}=F_{es}$ ($V_{es}-V_o$). 8Br-cGMP was administered as described above and ESPVR measurements were taken every 15 minutes for 2 hours. To gauge the effect of a known negative inotrope, an intravenous bolus of esmolol (1 mg/kg) was given after the 2 hour period, and the same measurements were obtained. The other cyclic nucleotides were administered similarly.

Calculations and Statistics: CVP, PCWP, MAP, MPAP, and CO were recorded. Pulmonary vascular resistance (PVR, dynes.sec/$cm^5$) and systemic vascular resistance (SVR, dynes.sec/$cm^5$) were calculated as follows; PVR=80 (MPAP−PCWP)/CO; SVR=80 (MAP−CVP)/CO. For each animal, the PVR and SVR were calculated under the baseline conditions, and when consistent serial measurements were obtained, pulmonary hypertension was induced using one of the methods. PVR and SVR in the hypertensive state prior to administration of the test compound were compared to the lowest PVR and SVR values recorded after administration of the test compound. Each animal contributed a single data point to the statistical calculations. Pre- and post-treatment values were compared using the paired Student t-test to discriminate significant differences. Data was considered statistically significant if p<0.05. The effect of 8Br-cGMP on arterial oxygenation was recorded simultaneously with the greatest drop in PVR. Time course data were analyzed using ANOVA, using Tukey's test to discriminate significant differences between group means. Data was considered significant if p<0.05.

EXPERIMENTAL RESULTS

8-Br-cGMP

Figure 1B:
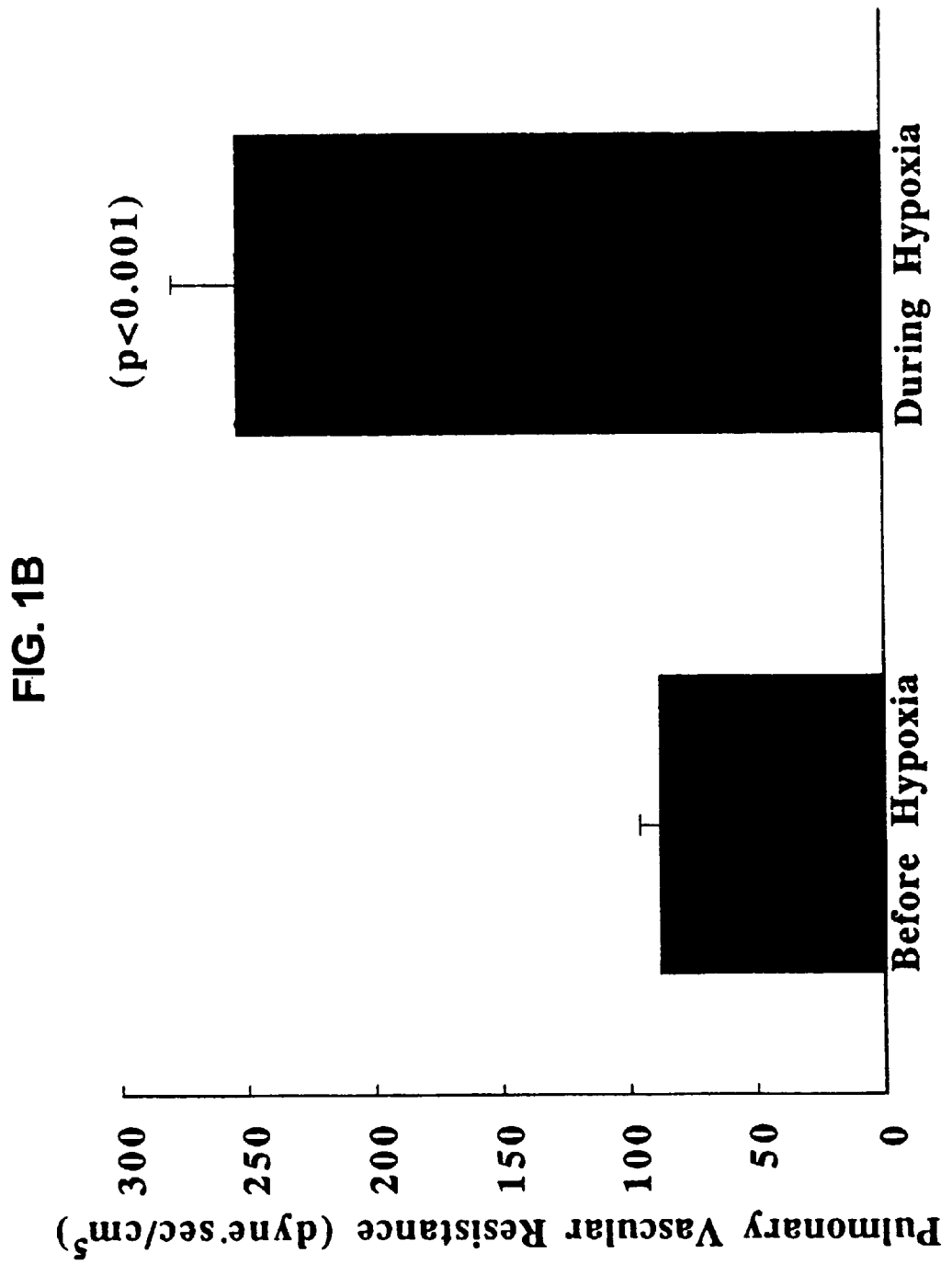
Figure 1C:
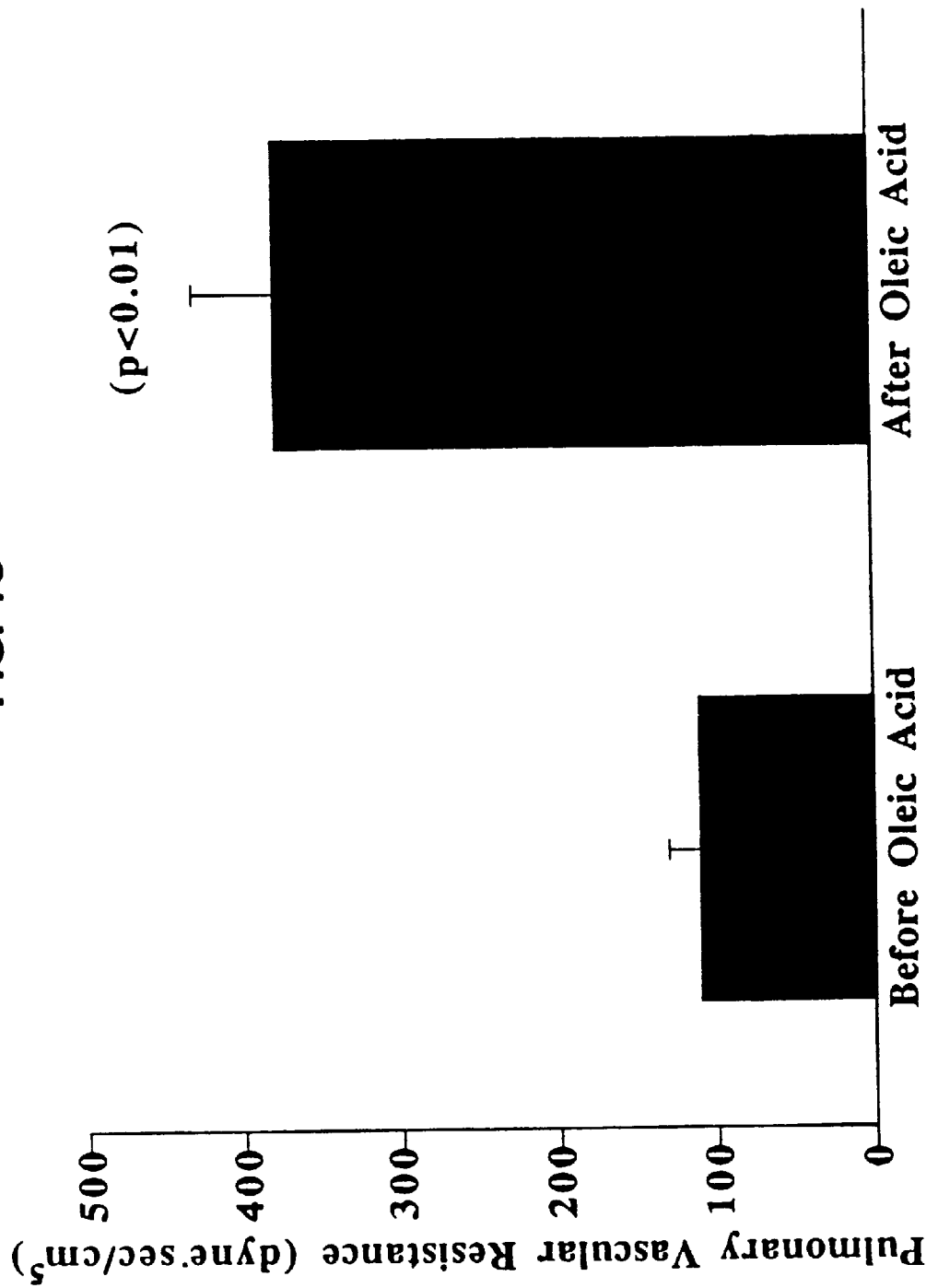
Figure 4A:
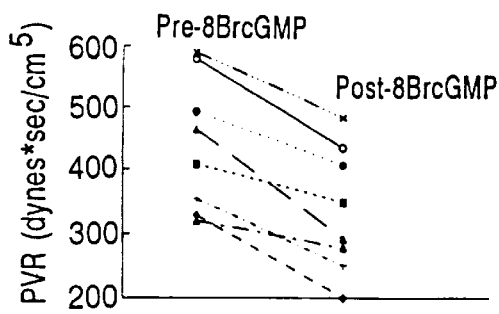
FIGS. 4A–4B: Hemodynamic data in the thromboxane analog model of pulmonary hypertension before and after inhalation of 8Br-cGMP. Each symbol represents a single animal.
Figure 4B:
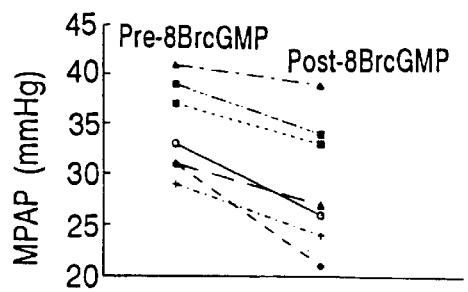
Figure 4C:
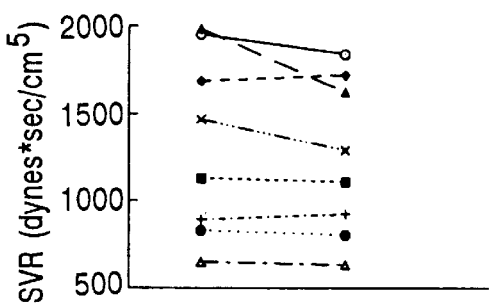
Figure 4D:
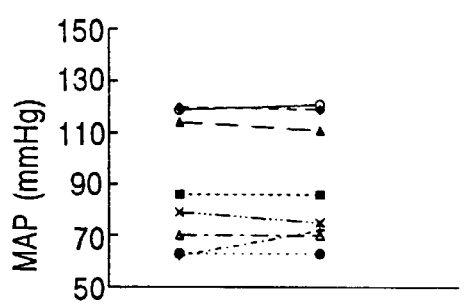
Figure 4E:
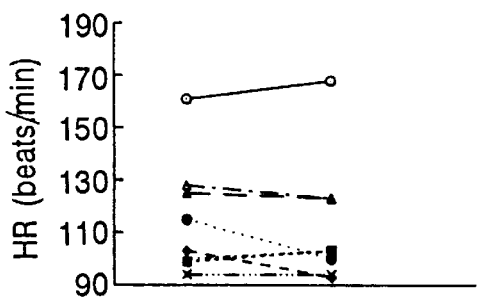
Figure 4F:
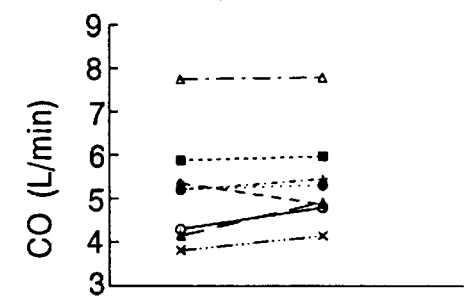
Figure 4G:
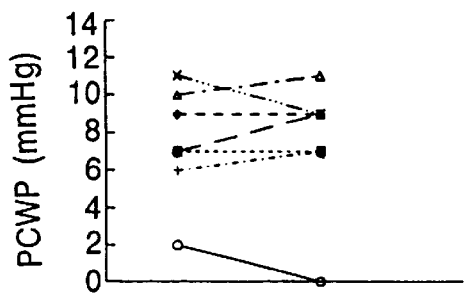
Figure 4H:
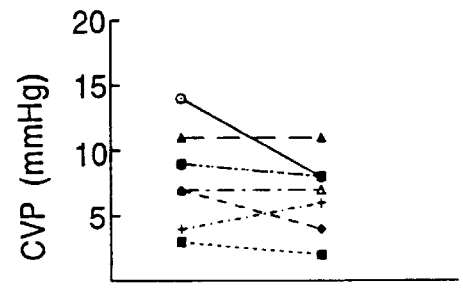

Three porcine models of pulmonary hypertension were established: a vasoconstrictor model using an intravenous infusion of the thromboxane $A_2$ analog (n=9), a model of hypoxia-induced pulmonary vasoconstriction (n=8), and a model of ARDS created by intravenous injection of oleic acid (n=6). In each of these models, baseline hemodynamic measurements were initially recorded and then pulmonary hypertension was induced as described (FIGS. 1A–1C). In the thromboxane model, PVR increased by 364±8.8% (p<0.001 vs. baseline). In the hypoxia model PVR increased by 187±8.4% vs. baseline (p<0.001). The ARDS model demonstrated an increase in PVR following oleic acid administration by 241±17% (p<0.01).

The effects of an inhaled membrane-permeable analog of cGMP, 8Br-cGMP, on PVR and SVR were studied in each of the three models of pulmonary hypertension to determine whether this compound and method of administration might confer relative selectivity for the pulmonary vasculature. Hemodynamic measurements of a representative animal in the thromboxane model are shown after physiologic saline inhalation (FIGS. 2A–2E) and 8Br-cGMP inhalation (FIGS. 2F–2J). In the thromboxane model, the decrease in PVR after inhalation of 8Br-cGMP was significant when compared with inhalation of the physiologic saline vehicle (−23.9±3.8% vs. 7.6±3.5%, p<0.001). PVR dropped significantly more than did the corresponding SVR (23.9% vs. 1.1%, respectively p<0.01) following inhalation of 8Br-cGMP (FIG. 3A). To establish that this selective response was not simply due to delayed distribution of the compound to the systemic vasculature, the maximal declines in PVR and SVR were recorded following administration (FIG. 3B). This comparison demonstrated that even when the maximal decline in SVR was recorded, inhaled 8-Br-cGMP remains a relatively selective pulmonary vasodilator.

The drop in PVR in the thromboxane analog model following inhaled 8Br-cGMP was predominantly due to its effects to decrease mean pulmonary arterial pressure although there was an improvement in cardiac output in some animals. Other hemodynamic variables (including PCWP, HR, MAP, CVP, and SVR) remained relatively stable (FIGS. 4A–4H).

Figure 5:
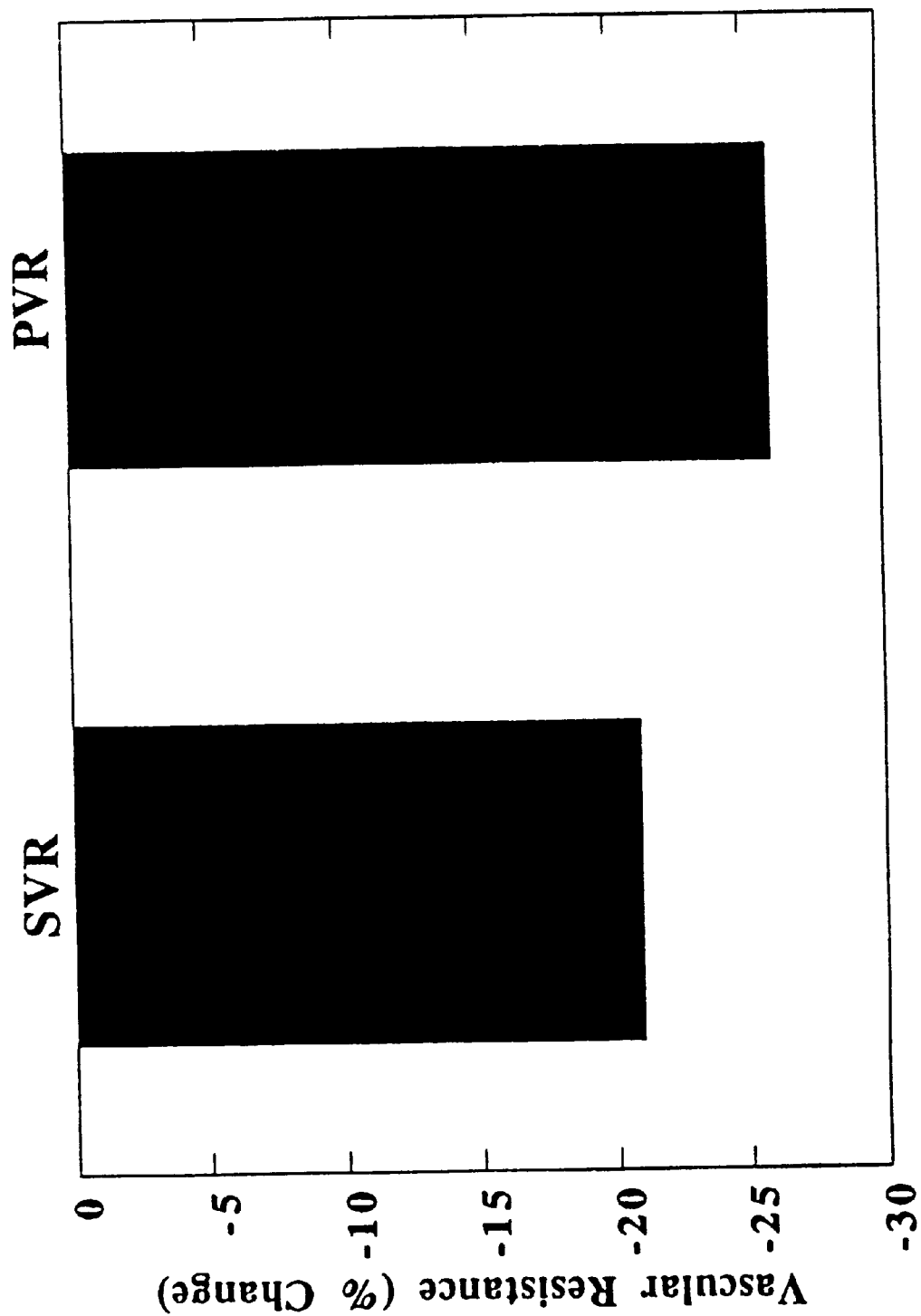
FIG. 5: The maximal % decreases in SVR and PVR after intravenous administration of 8Br-cGMP (300 μg/kg) in the thromboxane analog model.

To assess the relative selectivity of inhaled 8Br-cGMP in reducing PVR compared with SVR, the thromboxane model was used to measure vascular resistance changes in response to intravenously administered 8Br-cGMP (FIG. 5). The decrease in PVR (−26%) was similar to that obtained by giving the drug via the inhaled route (−24%), but the SVR decreased much more after intravenous compared with inhaled 8Br-cGMP (−21% vs. −5%).

To determine whether the pulmonary vascular response to inhaled 8-Br-cGMP was dependent on a specific model of pulmonary hypertension, pigs were ventilated with a hypoxic gas mixture, and hemodynamic measurements were obtained as in the thromboxane model. As in the thromboxane model, PVR in this model dropped significantly more than did the corresponding SVR (23.3% vs. 8.7%, respectively p<0.01) following inhalation of 8-Br-cGMP (FIG. 6A). These results are similar even when maximal decline in PVR and SVR are compared (FIG. 6B). These data illustrate that the effects of inhaled 8-Br-cGMP are similar when two different models of pulmonary hypertension are studied.

Figure 7A:
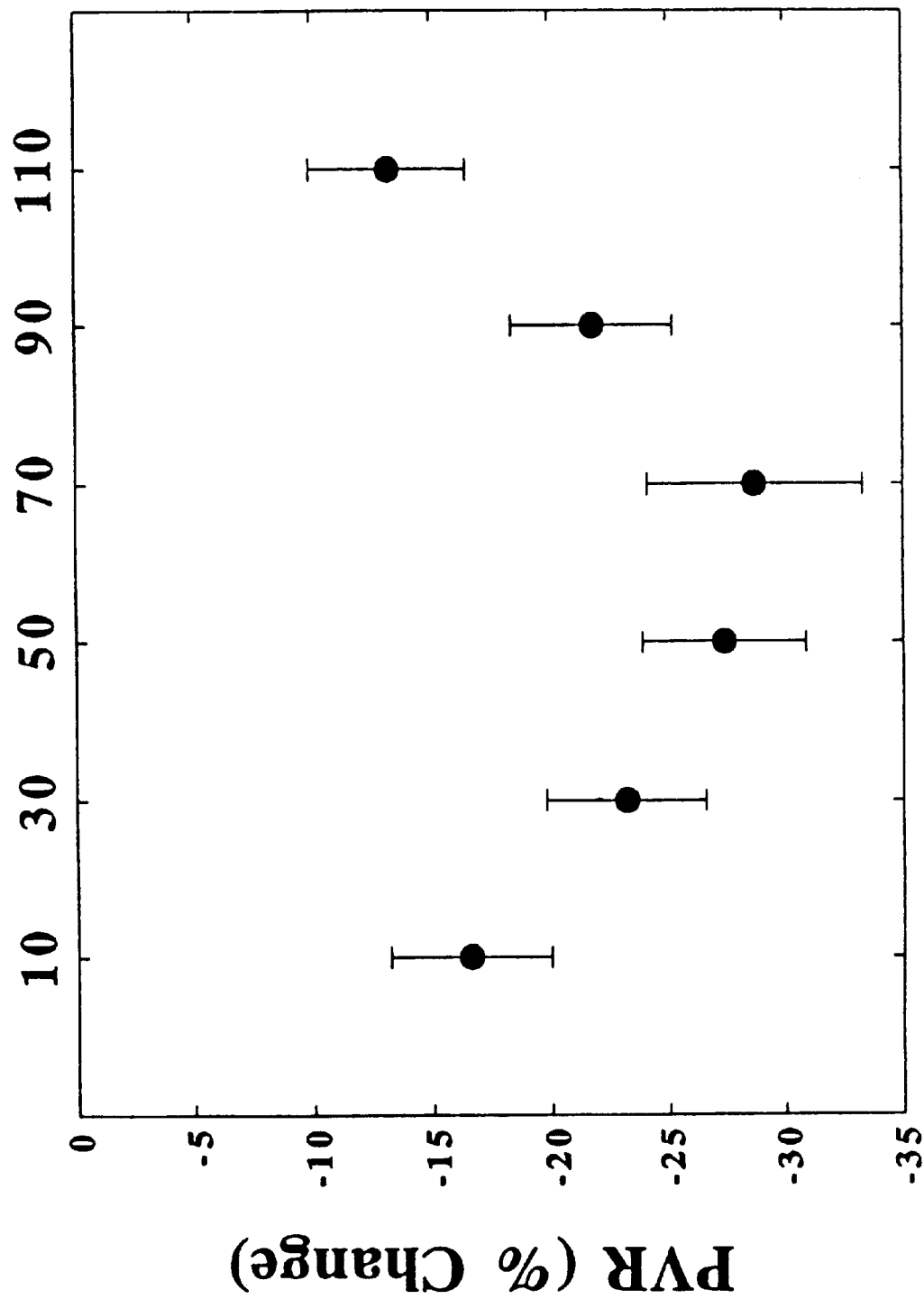
FIGS. 7A–7B: Effect of 8-Br-cGMP on pulmonary hypertension: time course and dose-response. (A) Time course of effect of 8-Br-cGMP on PVR in the thromboxane analog and hypoxia models of pulmonary hypertension. Peak effect of 8-Br-cGMP to lower PVR is observed approximately 70 minutes following inhalation. Times shown represent measurements taken at the indicated times±minutes. (B) Dose-response of inhaled 8-Br-cGMP on PVR demonstrates maximal reduction in PVR at doses between 2–20 $\mu$g/kg. ($p<0.001$ vs physiologic saline. control).
Figure 7B:
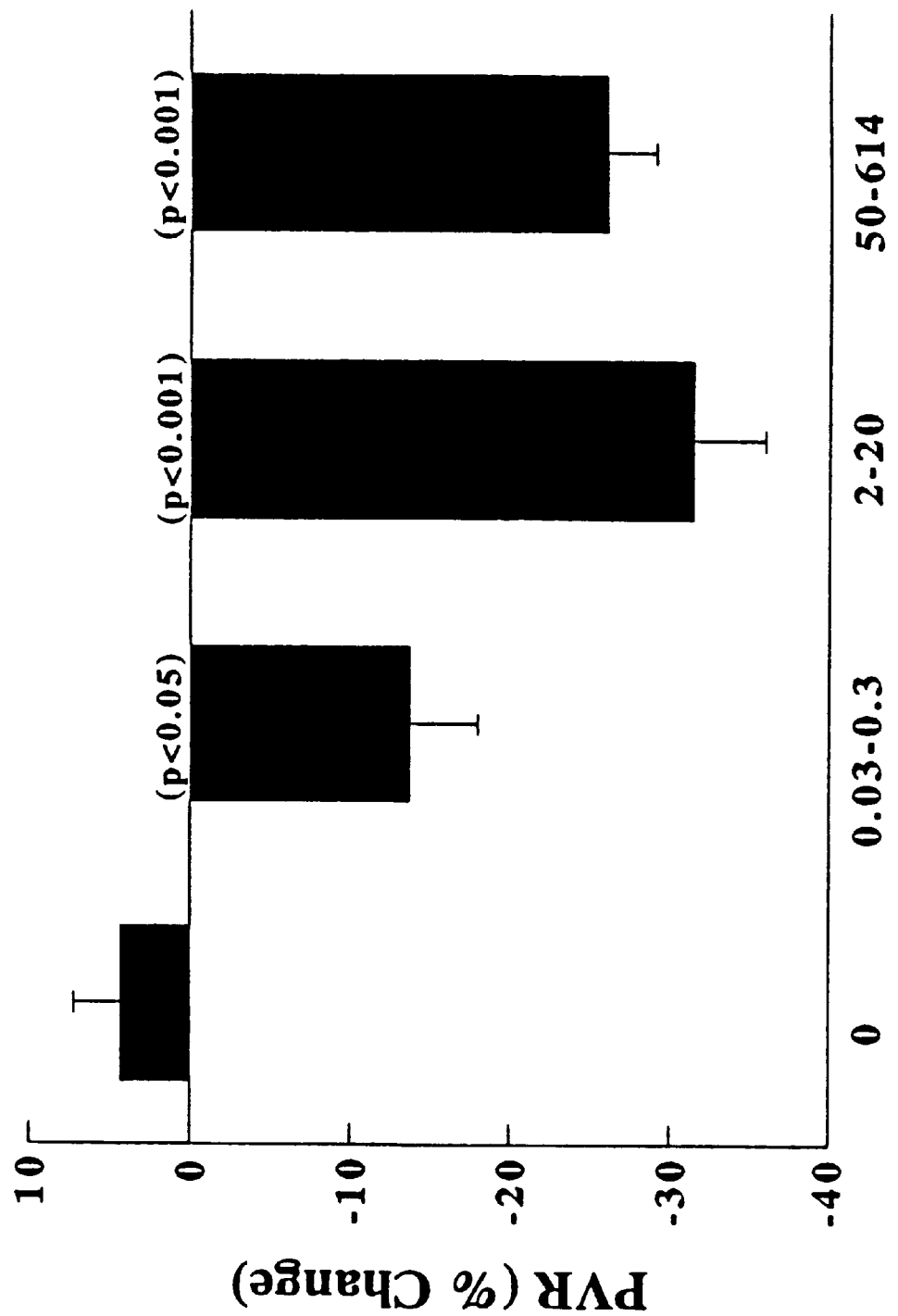

The effects of inhaled 8-Br-cGMP are time-dependent, with maximal effect occurring approximately 70 minutes after administration. These time course experiments consistently demonstrated both an initial drop in PVR as well as a gradual return to the pulmonary hypertensive baseline (FIG. 7A). 8-Br-cGMP was effective over a broad range of doses, with doses as low as 0.03 µg/kg showing a pulmonary vasodilator effect, with a maximal effect seen with doses between 2–20 µg/kg (31.5±4.5% drop in PVR, p<0.001). (FIG. 7B).

Because NO has been shown to reduce PVR in human ARDS (6), experiments were performed to investigate whether 8-Br-cGMP might act similarly in a porcine model of ARDS (n=5). Oleic acid administration caused a marked increase in PVR (FIG. 1C), a drop in arterial oxygenation (on 100% oxygen, $PO_2$ declined from 525±21 torr to 61±7 torr over the course of 5 hours), and development of edematous lungs as evidenced by copious pulmonary secretions and increased lung weights at autopsy (6.3±1.6 mg/kg control vs. 13.3±1.4 mg/kg oleic acid). In this model, 8Br-cGMP decreased PVR significantly when compared with normal saline control (−34.3±8% vs. 3.35±1.5%, p<0.05). Compared with the other models, the decrease in PVR compared with SVR only tended towards pulmonary selectivity (34±8% decline vs. 27±11% decline for PVR and SVR, respectively, p=NS).

A comparison of the pulmonary vasodilating effects between 8Br-cGMP and NO was performed in the thromboxane (n=3) and oleic acid (n=3) models. In the thromboxane model, NO reduced PVR by 46.8±7.3% while inhaled 8Br-cGMP decreased PVR by 23.9% (p=NS). In the oleic acid model, 8-Br-cGMP tended to be more effective than NO at reducing PVR (−34.3±8.0% for 8-Br-cGMP vs. −18.7±4.5% for oleic acid, p=NS).

Although cardiac outputs increased slightly following 8-Br-cGMP (FIGS. 4A–4H), data of others (11–14) suggests that stimulation of the NO pathway may result in depression of myocardial contractility, which would be of clinical concern in patients with compromised ventricular function. The effect of inhaled 8-Br-cGMP on load-independent measures of cardiac contractility was investigated using a left ventricular conductance catheter and varying preload by controlling blood return via the inferior vena cava. To establish a control for this detection method, intravenous esmolol (40 mg) was given as a bolus injection, which demonstrated a clear-cut negative inotropic effect (FIGS. 8A–8C). In contrast, inhalation of 8Br-cGMP at a dose associated with a pulmonary vasodilator effect (30 µg/kg) did not alter ventricular performance (n=2) (FIGS. 8A–8C).

Sp-8-Br-cGMPS

Figure 9:
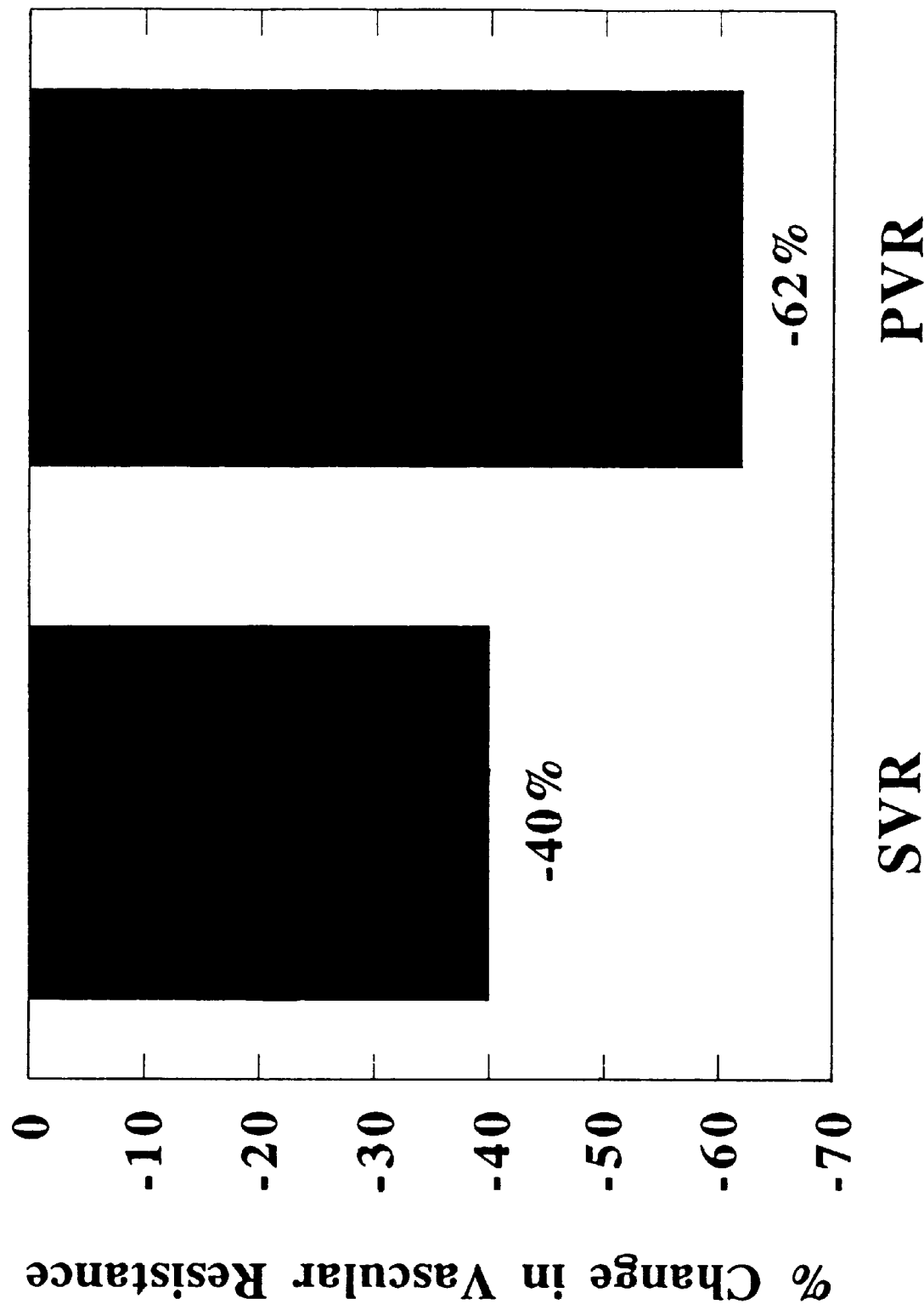
FIG. 9: Percent change in SVR and PVR upon administration of Sp-8-Br-cGMPS (Thromboxane model).

Sp-8-Br-cGMPS was administered in the thromboxane model as above, resulting in a drop in PVR of 62%. However, SVR also decreased by 40%. Thus, in this model, Sp-8-Br-cGMPS had a strong effect on PVR, also demonstrating relative selectivity (FIG. 9).

Permeabilizing Solvents

Figure 10:
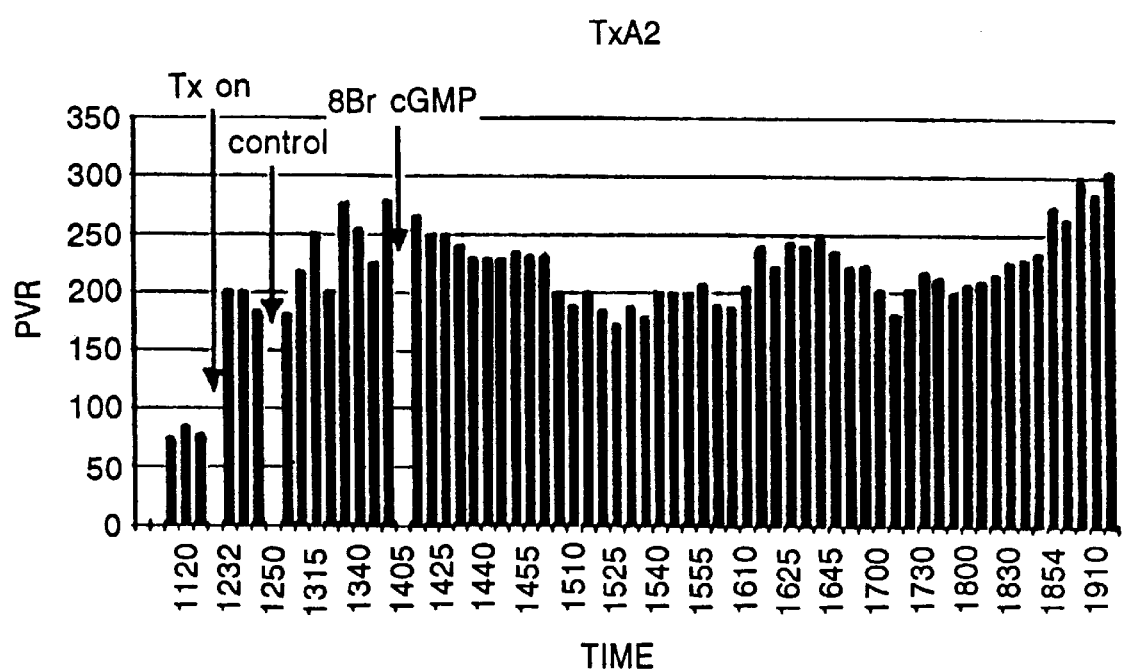
FIG. 10: Effect of inhalation of 8-Br-cGMP solubilized in DMSO.

Although the experiments consistently demonstrate that 8-Br-cGMP selectively lowers PVR, the magnitude of this effect can be enhanced by increasing the ability of 8-BrcGMP to penetrate cell membranes. This has been done by solubilizing the 8-Br-cGMP in the solvent dimethyl sulfoxide (DMSO), with similar administration as above. When 8-Br-cGMP is mixed in this way and subsequently inhaled, it causes a 37% drop in PVR in the thromboxane-induced pulmonary hypertension model (FIG. 10).

Dibutyryl cAMP

Figure 11:
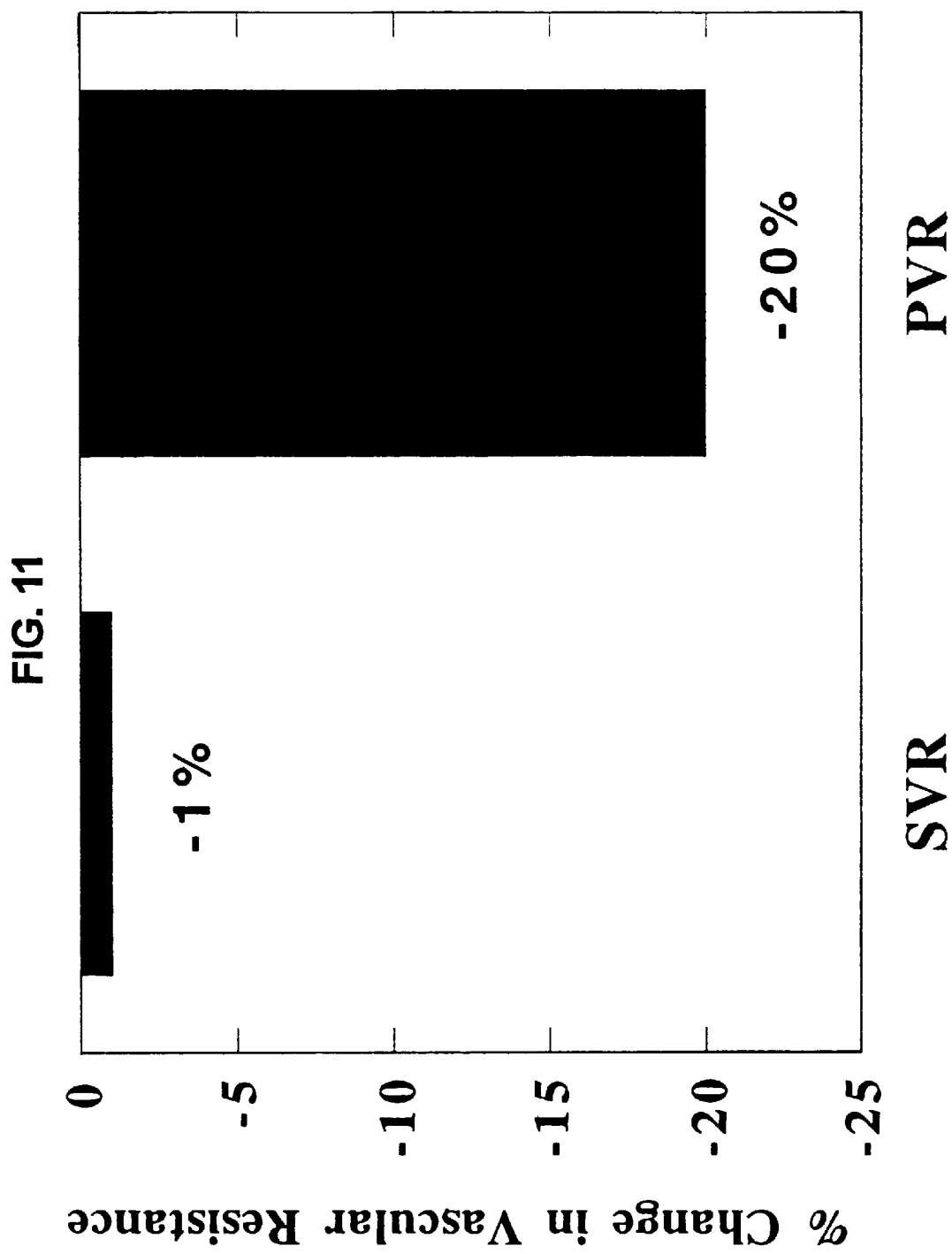
FIG. 11: Percent change in SVR and PVR upon administration of dibutyryl-cAMP solubilized in DMSO (Thromboxane model).

Dibutyryl cAMP solubilized in DMSO was administered in the thromboxane model. Dibutyryl cAMP caused a 20% drop in PVR with little effect on systemic vascular resistance (FIG. 11).

8-Br-cAMP

Figure 12:
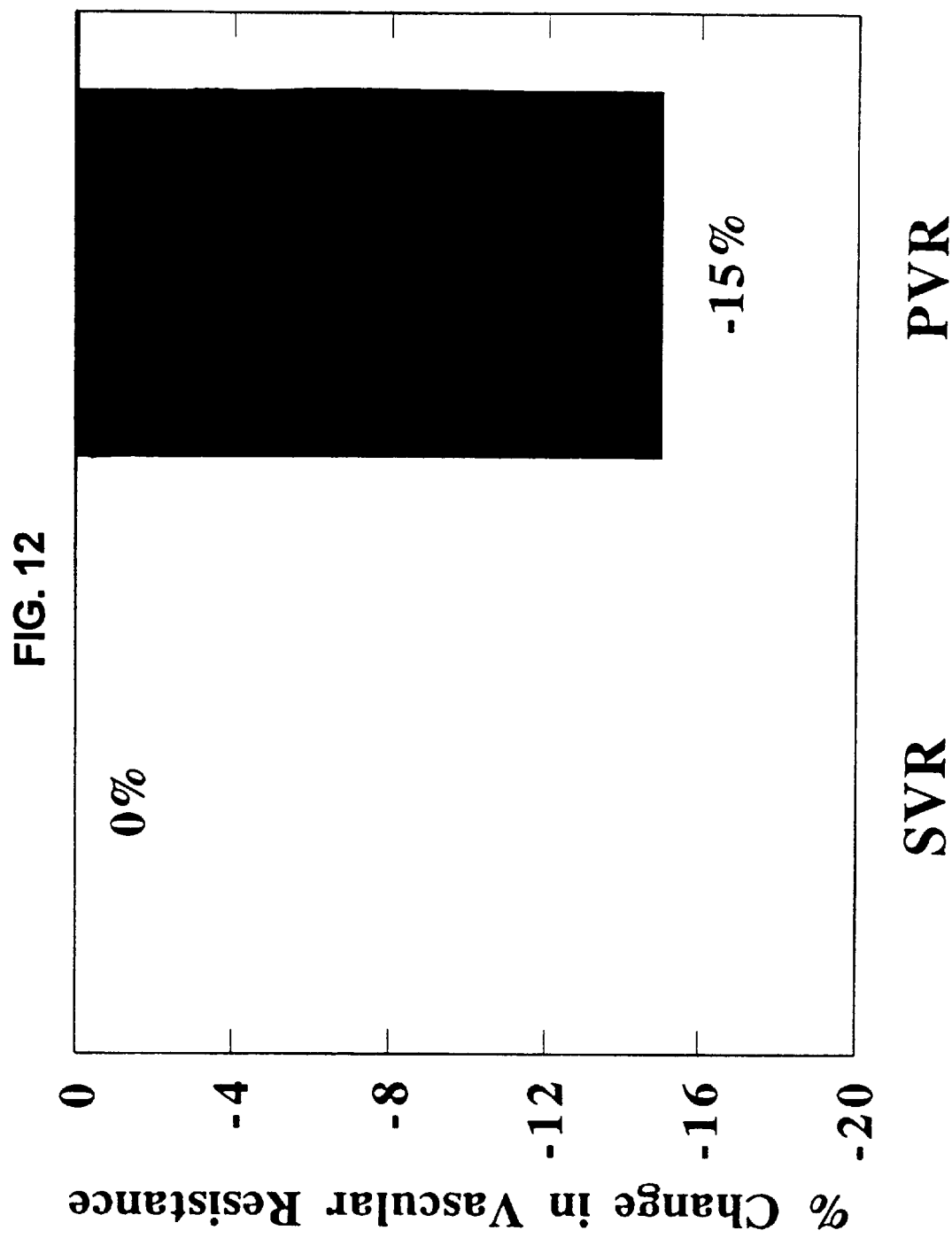
FIG. 12: Percent change in SVR and PVR upon administration of 8-Br-cAMP (Hypoxia model).

8-Br-cAMP was administered in the hypoxia model as described. Pulmonary vascular resistance was selectively reduced with no measurable effect on systemic vascular resistance (FIG. 12).

Phosphodiesterase Inhibitors

To exclude a role for activation of purinergic receptors in the lungs (17) to explain how 8-Br-cGMP might cause a decline in PVR, inhaled 8-bromoguanosine-5'-monophosphate was administered in the thromboxane analog model and found to have no effect on PVR or SVR (n=2). Because NO and 8-Br-cGMP drop PVR, this implicated a role for cGMP in pulmonary vasodilation. To explore this possibility further, the phosphodiesterase inhibitor M & B 22948 (Zaprinast), which specifically inhibits the degradation of endogenous cGMP was administered via inhalation. In this pilot study of two animals, Zaprinast decreased PVR more than SVR (41±27% decrease vs 20±11% decrease, respectively). These data suggest that elevating endogenous levels of cGMP or inhaling cGMP analogs can effectively lower pulmonary vascular resistance.

Figure 13:
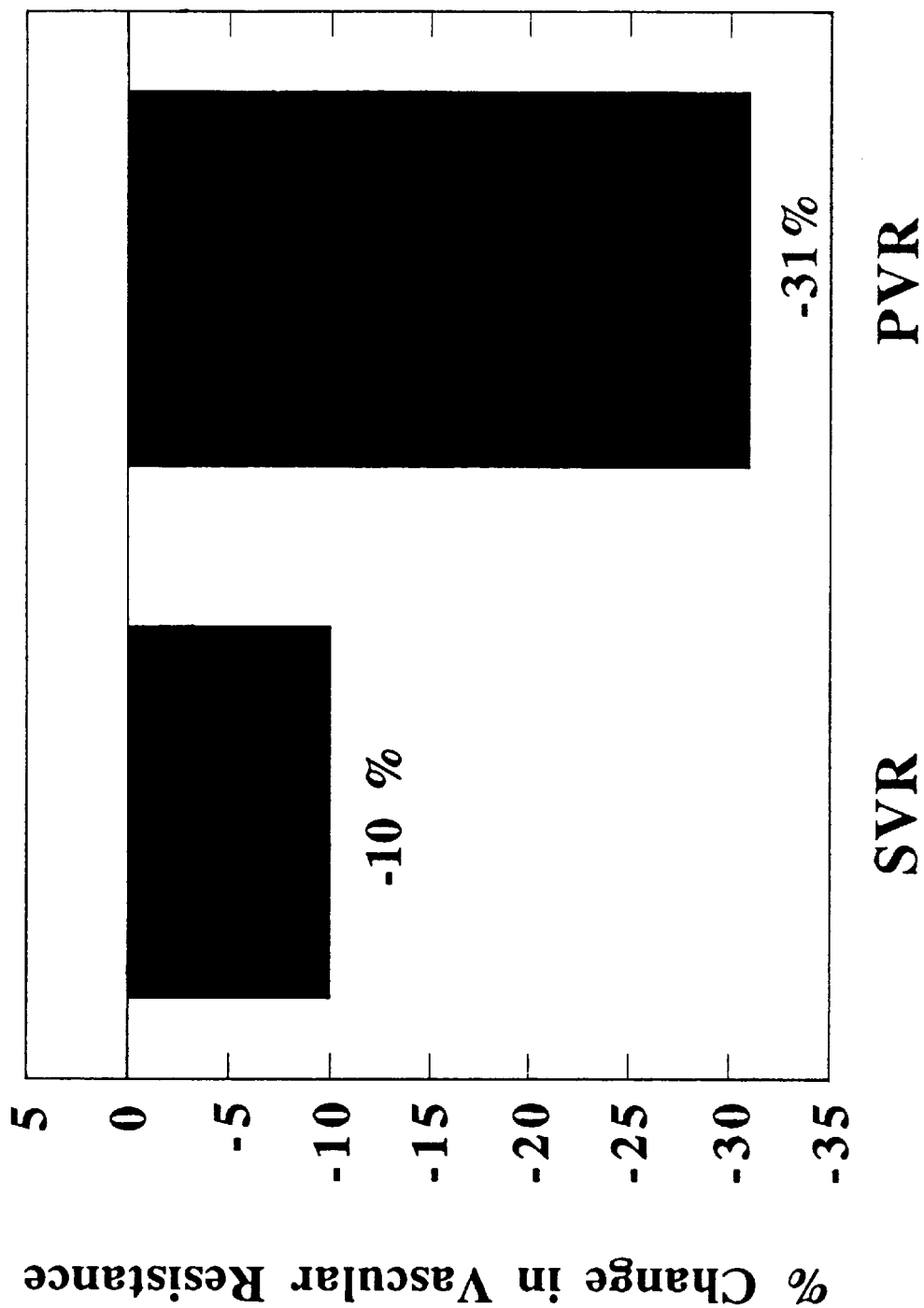
FIG. 13: Percent change in SVR and PVR upon administration of IBMX (Hypoxia model).

It was further hypothesized that inhalational administration of a compound that retards degradation of cGMP and cAMP would result in higher levels of the endogenous compounds, thereby lowering pulmonary pressures. To test this hypothesis, phosphodiesterase inhibitor (phosphodiesterases break down cAMP and cGMP, and can be selective for either compound or break down both) called isobutylmethylxanthine (IBMX) was administered. The inhalational administration of IBMX caused a drop in pulmonary vascular resistance (FIG. 13) with much less of an effect on systemic vascular resistance (in the hypoxia model). This indicates that not only can there be benefit by inhaling the cyclic nucleotides themselves, but there can be benefit by inhaling a compound which retards their degradation.

EXPERIMENTAL DISCUSSION

Both primary and secondary pulmonary hypertension are associated with extremely high morbidity and mortality. Although many therapeutic agents have been tried in order to lower the elevated pulmonary vascular resistance associated with these conditions no agent has been found effective (1,18–20). The efficacy of these agents is uniformly limited by the nonspecific nature of the vasodilation, in that systemic vascular resistance is often lowered to a similar or greater degree than pulmonary vascular resistance, occasionally causing a precipitous drop in blood pressure resulting in patient death (1,19,21). A drug is considered to be clinically effective in pulmonary hypertension if it can lower PVR more than it lowers SVR, i.e., is relatively selective for the pulmonary vasculature (1). Since most patients with chronic pulmonary hypertension die from right ventricular failure, a goal of drug therapy would be reduction of pulmonary artery pressures and calculated PVR, and normalization of cardiac output (20). In 1991, reports began to emerge concerning the use of an inhaled gas, nitric oxide, to provide selective pulmonary vasodilation in pulmonary hypertension (2,3). Rationale for the use of nitric oxide to treat pulmonary hypertension is based upon its ability to stimulate soluble guanylyl cyclase found in smooth muscle cells throughout the vasculature, leading to an increase in intracellular cGMP and subsequent vasodilation (22). Because nitric oxide binds rapidly and avidly to hemoglobin, it preferentially dilates the pulmonary vasculature. Recent clinical studies in ARDS demonstrate that this therapy is likely to benefit patients during continuous administration (6). There are practical and theoretical concerns to NO administration however: being a gas, special delivery equipment is required, and its effects are dependent on continuous administration (3,6); its free radical structure makes it highly reactive with oxygen atoms, producing toxic peroxynitrite metabolites (4,5); and its carcinogenic potential is yet to be defined, but it has been reported to produce a positive Ames test for mutagenicity (4).

To overcome these limitations, it was hypothesized that administration of a stable lipid soluble analog of cGMP (8-Br-cGMP) might have similar beneficial pulmonary vasodilating effects. In isolated lung models, this agent administered intravenously effectively reduces hypoxia-induced pulmonary vasoconstriction (23). Although others have given 8-Br-cGMP intravenously (24), this method of administration would confer no differential benefit upon the pulmonary vasculature. Because 8-Br-cGMP is in itself not specific for the pulmonary cGMP-dependent protein kinase, it was hypothesized that inhalation of aerosolized 8-Br-cGMP would produce the highest possible pulmonary concentrations, thereby conferring selective reduction of pulmonary vascular resistance.

Three models of pulmonary hypertension were established. Because thromboxane is thought to play a role in pulmonary hypertension in diseases as varied as scleroderma, systemic lupus erythematosus, cirrhosis of the liver, and pulmonary emboli (25–33), the thromboxane analog U-46619,9,11-dideoxy-11α,9α-epoxymethanoprostaglandin $F_{2\alpha}$ (10) was infused to induce pulmonary hypertension. This model was well suited to measuring the effects of pharmacologic intervention, because after a 60–90 minute period of stabilization during which constant doses of this analog were infused, hemodynamic measurements remained stable (see FIG. 2A–E). In addition, others have shown that endothelium-derived relaxing factor (nitric oxide or related compounds) plays a significant role in blunting the pulmonary response to vasoconstrictors such as thromboxane (10), making this model ideal to test the effects of a cGMP analog. These studies demonstrate that inhalation of aerosolized 8-Br-cGMP causes a significant decline in pulmonary vascular resistance, with minimal effects on systemic vascular resistance and left ventricular contractile strength. After a single dose of 8-Br-cGMP, the drop in PVR was over 50% of that achieved with continuous nitric oxide inhalation under identical conditions. In contrast with NO, however, the effects of 8-Br-cGMP were longer-lived, lasting up to 2 hours (nitric oxide's effects were completely gone within 4 minutes of discontinuation).

Because many clinical conditions are associated with hypoxemia, the effects of ventilation with a hypoxic gas mixture were investigated. Hypoxia-induced vasoconstriction has been well described (34,35), and is frequently used as a model system to study pulmonary hypertension (3,36). The levels of hypoxia used in the present study (inhaled 9–10%) were chosen as the minimal levels tolerated by the animals without the development of metabolic acidosis (lowest average pH 7.36±0.02) or circulatory collapse. Because small variations in inspired $O_2$ caused large fluctuations in PVR, inhaled $O_2$ was continuously monitored with frequent sampling of arterial $pO_2$ ($pO_2$ 36.5±2.2 mmHg at lowest PVR value). As in the thromboxane model, aerosolized 8-Br-cGMP caused a selective reduction in PVR. For both the thromboxane-induced and hypoxia-induced pulmonary hypertension models, the effects of inhaled 8-Br-cGMP were time- and dose-dependent, with maximal effects seen at about 70 minutes following administration, at doses between 2–20 µg/kg. This data suggests that clinical conditions with elevated pulmonary vascular resistances associated with hypoxemia (such as congenital heart disease, sleep apnea syndrome, or end-stage pulmonary disease (37)) may potentially benefit from inhalation of compounds augmenting cGMP levels.

As a third model to test the effects of inhaled 8-Br-cGMP, an ARDS-like condition was created by intravenous injection of oleic acid (38–42), which manifested as elevated PVR, pulmonary exudation, and hypoxemia, characteristic of human ARDS. These characteristics are similar to those described by others using this same model (38–42). Because the permeability of the lungs is markedly increased following oleic acid administration (41), corroborated by increased lung weights in the oleic acid-treated pigs compared to controls in our experiments, it is possible that inhalation of 8-Br-cGMP results in greater systemic delivery in this model compared with the thromboxane- and hypoxia-induced pulmonary hypertension models. This may explain why SVR declined more in the ARDS model following 8-Br-cGMP administration than in the other models. This is consistent with the observation that intravenous infusion of 8-Br-cGMP causes systemic vasodilation (24), explaining why the trend of 8-Br-cGMP as a selective pulmonary vasodilator in this model did not achieve statistical significance. Although NO has been shown to improve oxygenation in human ARDS (6), its effect in this model was minimal ($pO_2$ changed from 74 to 76 mm Hg after 10 minutes of continuous administration of NO 50 ppm); the effects of inhaled 8-Br-cGMP on systemic oxygenation in our study were similarly unimpressive. This may have been due to the fulminant nature of the oleic acid-induced ARDS, and the rapid deterioration of the pig over the course of each experiment. In a control experiment in which oleic acid was given and effects on oxygenation were observed without 8-Br-cGMP, oxygenation rapidly deteriorated. This decline in arterial oxygenation over time may obscure a small increase caused by an experimental therapy which takes over an hour to achieve peak effect.

There is a theoretical concern that stimulation of the nitric oxide pathway might depress myocardial contractility, which would be of clinical concern in patients with cor pulmonale. Depression of myocardial contractility has been ascribed to nitric oxide production (11–13), and 8-Br-cGMP itself has been shown to exert a moderate negative inotropic effect on isolated ferret cardiac muscle (14), so it was important to measure the effect of inhaled 8-Br-cGMP on load-independent measures of myocardial contractility. Because load-independent measures of right ventricular performance are difficult to obtain and remain to be validated (43), this data uses pressure-volume loops to construct load-independent measures of left ventricular function following inhalation of 8-Br-cGMP. In this study, inhalation of 8-Br-cGMP at an effective pulmonary vasodilating dose has no effect on left ventricular ESPVR suggesting no effect on contractile strength.

To understand the mechanism whereby 8-Br-cGMP acts as a pulmonary vasodilator, 8-Br-guanosine 5'monophosphate was administered to exclude a role for puringergic receptor activation at pharmacologic doses. These receptors are widely distributed in the pulmonary vasculature and are known to affect smooth muscle tone (17). This compound had no effect in decreasing PVR when given at a dose at which 8-Br-cGMP demonstrates a clear-cut decline in PVR (270 µg/kg). This suggests that 8-Br-cGMP's ability to reduce PVR is related to its actions as a second messenger cyclic nucleotide.

In conclusion, inhalation of 8-Br-cGMP provides selective pulmonary vasodilation in two clinically relevant models of pulmonary hypertension. These effects are likely to be mediated by its effects as a second messenger cyclic nucleotide. The combination of an agent which stimulates the NO/cGMP pathway with a directed method of delivery (such as inhalation) suggests a broad range of pharmacologic possibilities for the treatment of diseases resulting in pulmonary hypertension.

REFERENCES FOR FIRST SERIES OF EXPERIMENTS

1. Packer, M. Vasodilator therapy for primary pulmonary hypertension. Ann. of Int. Med. 1985. 103(2) 258–270.

2. Pepke-Zaba J. Higenbottam T W, Dinh-Xuan A T, Stone D, and Wallwork J. Inhaled nitric oxide as a cause of selective pulmonary vasodilation in pulmonary hypertension. Lancet. 1991. 338(8776) 1173–1174.

3. Frostell C, Fratacci M, Wain J, Jones R, and Zapol W. Inhaled nitric oxide: a selective pulmonary vasodilator reversing hypoxic pulmonary vasoconstriction. Circ. 1991. 83(6) 2038–2047.

4. Arroyo P L, Hatch-Pigott V, Mower H F, Cooney R V. Mutagenicity of nitric oxide and its inhibition by antioxidants. Mutation Research. 1992; 281: 193–202.

5. Beckman J S, Beckman T W, Chen J, Marshall P A, Freeman B A. Apparent hydroxyl radical production by peroxynitrite: Implications for endothelial injury from nitric oxide and superoxide. Proc. Natl. Acad. Sci. USA. 1990; 87: 1620–1624.

6. Rossaint R, Falke K, Lopez F, Slama K, Pison U, Zapol W. Inhaled nitric oxide for the adult respiratory distress syndrome. N. Engl. J. Med. 1993. 328(6) 399–405.

7. Lincoln T M, and Cornwell T L. Intracellular cyclic GMP receptor proteins. FASEB J. 1993; 7: 328–338.

8. Murad F. Cyclic guanosine monophosphate as a mediator of vasodilation. J. Clin. Invest. 1986; 78: 1–5.

9. Kuo J F. Molecular and physiopathologic aspects of mammalian cyclic GMP-dependent protein kinase. Ann. Rev. Pharmacol. Toxicol. 1978; 18: 341–355.

10. Fineman J, Chang R, Soifer S. EDRF inhibition augments pulmonary hypertension in intact newborn lambs. Am. J. Physio. 1992 262(3) H1365–H1371.

11. Balligand J-L, Ungureanu D, Kelly R A, Kobzik L, Pimental D, Michel T, Smith T W. Abnormal contractile function due to induction of nitric oxide synthesis in rat cardiac myocytes follows exposure to activated macrophage-conditioned medium. J. Clin. Invest. 1993; 9: 2314–2319.

12. Brady A J B, Poole-Wilson P A, Harding S E, Warren J B. Nitric oxide within cardiac myocytes reduces their contractility in endotoxemia. Am. J. Physiol. 1992; 263: H1963–H1966.

13. Finkel M S, Oddis C V, Jacob T D, Watkins S C, Hattler B G, Simmons R L. Negative inotropic effects of cytokines on the heart mediated by nitric oxide. Science. 1992; 257(5068): 387–389.

14. Shah A M, Lewis M J, Henderson A H. Effects of 8-Bromo-cyclic GMP on contraction and on inotropic response of ferret cardiac muscle. J. Mol. Cell Cardiol. 1991; 23: 55–64.

15. Baan J, van der Velde E T, DeBruin H G; Smeenk G J, Koops J, Van Dijk A D, Temmerman D, Senden J. Buis B. Continuous measurement of left ventricular volume in animals and humans by conductance catheter Circ. 1984; 70: 812–823.

16. Sagawa K. The ventricular pressure-volume diagram revisited. Circ. Res. 1978; 43: 677–687.

17. Dubyak G R. Signal transduction by $P_2$-purinergic receptors for extracellular ATP. Am. J. Respir. Cell Mol. Biol. 1991: 4: 295–300.

18. Priebe, H-J. Efficacy of vasodilator therapy in a canine model of acute pulmonary hypertension Am. J. Physiol. 1988. 255(5,pt.2). H1232–1239.

19. Weir E K, Rubin L J, Ayers S M, Bergofsky E H, Brundage B H, Detre K M, Elliott C G, Fishman A P, Goldring R M, Groves B M, Kernis J T, Koerner S K, Levy P S, Pietra G G, Reid L M, Rich S, Vriem C E, Williams G W, and Wu M. The acute administration of vasodilators in primary pulmonary hypertension. Experience from the National Institutes of Health registry on primary pulmonary hypertension. Am. Rev. Respir. Dis. 1989. 140(6) 1623–1630.

20. Rich. S. Should patients with pulmonary hypertension and increased pulmonary resistance be treated with vasodilators? Cardiovasc. Clin. 1990. 21(1) 265–274.

21. Partanen J. Nieminen M, Luomanmaki K. Death in a patient with primary pulmonary hypertension after 20 mg of Nifedipine (letter). NEJM. 1993; 329(11: 812–813.

22. Ignarro L. Biosynthesis and metabolism of endothelium-derived nitric oxide. Annu. Rev. Pharmacol. Toxicol. 30: 535–560, 1990.

23. Archer S, Rist K, Nelson D, DeMaster E, Cowan N, Weir E. Comparison of the hemodymanic effects of nitric oxide and endothelium-dependent vasodilators in intact lungs. 1990. J. Appl. Physiol. 68(2) 735–747.

24. Elsner D, Kromer E, and G Riegger. Hemodynamic, renal, and hormonal effects of 8-Br-cyclic GMP in conscious dogs with and without congestive heart failure. Journal of Cardiovascular Pharmacology. 1989. 14. 241–247.

25. Zamora C A, Baron D A, and Heffner J E. Thromboxane contributes to pulmonary hypertension in ischemia-reperfusion lung injury. J. Appl. Physiol. 1993 74(1) 224–229.

26. Christman B W, McPhereson C D, Newman J H, King G A, Bernard G R, Groves B M, and Loyd J E. An imbalance between the excretion of thromboxane and prostacyclin metabolites in pulmonary hypertension. N. Engl. J. Med. 1992. 327(2) 70–75.

27. Ostenden J, Hede R, Myreng Y, Ege T, and E. Holtz. Intravenous injection of Albunex microspheres causes thromboxane-mediated pulmonary hypertension in pigs, but not in monkeys or rabbits. Acta Physiol. Scand. 1992. 144(3) 307–315.

28. Byrick, R J, Mullen J B, Wong P Y, Kay J C, Wigglesworth D, and R J Doran. Prostanoid production and pulmonary hypertension after fat embolism are not modified by methylprednisolone. Ca. J. Anaesth. 1991. 385(5) 660–667.

29. Nuttal G A, Murray M J, and E J W Bowie. Protamine-heparin-induced pulmonary hypertension in pigs: effects of treatment with a thromboxane receptor antagonist on hemodynamics and coagulation. Anesthesiology. 1991. 74(1) 138–145.

30. Badesch D B, Orton E C, Zapp L M, Westcott J V, Hester J, Voelkel N F, and K R Stenmark. Decreased arterial wall prostaglandin production in neonatal calves with severe chronic pulmonary hypertension. Am. J. Respir. Cell. Mol. Biol. 1989. 1(6) 489–498.

31. Rostagno C, Gensini G F, Boncinelli S, Marsili M, Castellani S, Lorenzi P, Merciai V, Linden M, Chelucci G L, F. Cresci. The prominent role of thromboxane A2 formation on early pulmonary hypertension induced by oleic acid administration in sheep. Thromb. Res. 1990. 58(1) 35–45.

32. Pinheiro, J M, Pitt B R, and C N Gillis. Roles of platelet-activating factor and thromboxane in group B streptococcus-induced pulmonary hypertension in piglets. Pediatr. Res. 1989. 26(5) 420–424.

33. Seeger W, Walter H, Suttorp N, Muhly M, and S. Bhakdi. Thromboxane-mediated hypertension and vascular leakage evoked by low doses of *E. coli* hemolysin in rabbit lungs. J. Clin. Invest. 1989. 84(1) 220–227.

34. Morgan J M, Griffiths M, Du Bois R M, Evans T W. Hypoxic pulmonary vasoconstriction in systemic sclerosis and primary pulmonary hypertension. Chest. 1991; 99(3): 551–556.

35. Agusti A G N, Barbara J A, Roca J, Wagner P D, Guitart R, Rodriguez-Roison R. Hypoxic pulmonary vasoconstriction and gas exchange in exercise in chronic obstructive pulmonary disease. Chest. 1990; 97(2): 268–275.

36. Frostell C G, Blomqvist H, Hedenstierna G. Lundberg J, Zapol W M. Inhaled nitric oxide selectively reverses hypoxic pulmonary vasoconstriction without causing systemic vasodilation. Anesthesiology. 1993; 78(3): 427–434.

37. Textbook of internal medicine.

38. Halden E, Hedstrand U, and K Torsner. Oleic acid lung damage in pigs. Acta Anaesth. Scand. 1982. 26. 121–125.

39. Peltier L. Fat embolism III: the toxic properties of neutral fat and free fatty acids. Surgery. 1956. 40. 665.

40. Ashbaugh D, Uzawa T. Respiratory and hemodynamic changes after injection of free fatty acids. J. Surg. Res. 1968. 8. 417.

41. Hofman W, Ehrhart I, Granger W, and D Miller. Sequential cardiopulmonary changes after oleic-acid injury in dogs. Critical Care Med. 1985 13(1). 22–27.

42. Cabrera M, Nakamura G, Montague D, and R Cole. Effect of airway pressure on pericardial pressure. Am. Rev. Respir. Dis. 1989. 140. 659–667.

43. Burkhoff, Right heart conductance measurement Second Series of Experiments: Selective Reduction of Pulmonary Vascular Resistance by Inhalation of a cGMP Analog in a Porcine Model of Pulmonary Hypertension Summary Selective reduction of pulmonary vascular resistance remains a therapeutic goal for the treatment of pulmonary hypertension, but current therapeutic options remain severely limited. Although the gas nitric oxide (NO) selectively dilates the pulmonary vascular bed, it is difficult to administer, has a short biologic half-life, and is potentially toxic. It was hypothesized that stimulation of the NO pathway at the level of its second messenger, cyclic guanosine monophosphate (cGMP), by targeted pulmonary delivery of a membrane permeable, nonhydrolyzable cGMP analog would cause selective pulmonary vasodilation. Pulmonary hypertension was induced in 19 pigs by the intravenous infusion of a thromboxane $A_2$ analog (9,11-dideoxy-11α, 9α-epoxymethanoprostaglandin $F_{2\alpha}$). Inhaled 8-bromoguanosine 3':5'-cyclic monophosphate (8-Br-cGMP) lowered pulmonary vascular resistance in a time and dose-dependent manner, with maximal effect achieved after 20 minutes at doses as low as 0.3 µg/kg. Following 8-Br-cGMP inhalation (3.0 µg/kg), pulmonary vascular resistance declined by 25±3% (p<0.0001 vs. physiologic saline control), whereas there was no significant decline in systemic vascular resistance (4±6%); mean pulmonary arterial pressure declined (13±3%) and cardiac output increased (10±4%, p<0.001 for each parameter vs. physiologic saline control). In contrast, there was little change in mean arterial pressure. Pulmonary vascular resistance did not decrease after inhalation of noncyclic 8-bromoguanosine 5'-monophosphate, indicating that stimulation of the NO/cGMP pathway beyond the level of NO results in pulmonary vasodilation independent of stimulation of purinergic receptors. Inhaled 8-Br-cGMP had no deleterious effect on load independent measures of ventricular contractility, as shown by left ventricular pressure-volume loops generated at different preloads. Because selective pulmonary vasodilation was not observed following intravenous administration of 8-Br-cGMP, these studies demonstrate that targeted delivery of a cGMP analog by inhalation can selectively reduce pulmonary vascular resistance.

Introduction

Pulmonary hypertension is associated with significant morbidity and mortality, yet therapeutic options remain limited because agents which lower pulmonary vascular resistance (PVR) also lower systemic vascular resistance (SVR).[1] Inhalation of nitric oxide (NO) gas has been shown to selectively lower pulmonary vascular resistance in pulmonary hypertension,[2,3] but there are concerns about the formation of toxic products from the reaction of NO with oxygen,[4,5] logistic difficulties associated with delivery of a gas, the necessity of constant administration for continued effect due to the short biological half-life of NO,[3,6] and potential chromosomal effects.[4] Because NO exerts its vasodilating effects by increasing the cGMP content in vascular smooth muscle,[7,8] it was hypothesized that stimulation of the nitric oxide pathway using a nonhydrolyzable, membrane permeable analog of cGMP, 8-bromoguanosine 3':5'-cyclic monophosphate (8-Br-cGMP),[7,9] administered via inhalation would confer relative pulmonary selectivity and circumvent the difficulties and potential toxicities associated with the administration of NO. These studies used a porcine model of pulmonary hypertension to demonstrate the potential therapeutic usefulness of this approach.

Methods

This experimental protocol was approved by the Columbia University Institutional Animal Care and Use Committee. Female swine (Hampshire breed, 32–48 kg) were premedicated intramuscularly with ketamine (20 mg/kg) acepromazine (0.4 mg/kg), and glycopyrrolate (0.0075 mg/kg), intubated, anesthetized with isoflurane (constant exhaled level maintained at 1.3%), and paralyzed throughout the experiment using a curare infusion (9 mg/hr). The electrocardiogram was monitored (Datascope 2000, Datascope, Paramus, N.J.), and ventilation was controlled with an Ohmeda 7000 anesthesia ventilator (Ohmeda, Madison, Wis.) attached to an Ohmeda VMC anesthesia machine (BOC, W. Yorkshire, UK). Respiratory gases and airway pressures were monitored with an Ohmeda RGM 5250 analyzer (Ohmeda, Louisville, Colo.). An arterial catheter was inserted percutaneously into the femoral artery and the right external jugular vein was exposed via cutdown. An 8.5 introducer sheath (Arrow, Reading, Pa.) was inserted into the external jugular vein, followed by placement of a 7.5 F pulmonary artery thermodilution catheter (Baxter Edwards Critical Care, Irvine, Calif.) which was advanced to the pulmonary artery with hemodynamic monitoring. Systemic arterial, pulmonary arterial, central venous, and pulmonary capillary wedge pressures were transduced (Abbott, North Chicago, Ill.) at right atrial level, and displayed on Datascope 2000 monitors (Paramus, N.J.). Animal temperature was measured continuously by rectal probe and maintained by infrared heating lamps. Cardiac outputs were calculated using the thermodilution technique employing a cardiac output computer (Baxter Edwards Critical Care). Arterial and mixed venous blood gas measurements for pH, $pCO_2$ (mm Hg), $pO_2$ (mm Hg) and hemoglobin oxygen saturation were performed on a calibrated arterial blood gas analyzer (Nova Biomedical, Waltham, Mass.). Hematocrit was determined using a capillary microcentrifuge.

Hemodynamics were recorded at end expiration at baseline and every 10–15 minutes thereafter, and included measurements of heart rate (HR, beats/min), central venous pressure (CVP, mm Hg), pulmonary capillary wedge pressure (PCWP, mm Hg), mean arterial and mean pulmonary arterial pressures (MAP, MPAP, mm Hg), and thermodilution cardiac outputs (CO, L/min). PVR and SVR were calculated as described below. Three serial measurements of cardiac output using iced saline injection were averaged for each time point and were performed at the same point in the respiratory cycle for each experiment. When a stable baseline PVR was demonstrated, pulmonary hypertension was induced by continuous intravenous infusion of the thromboxane A2 analog 9,11-dideoxy-11α,9α-epoxymethanoprostaglandin $F_{2\alpha}$,[10] (Sigma Chemical Co., St. Louis, Mo.), at 0.07–0.11 µg/kg/min. After stable measurements of PVR in the hypertensive state were achieved, 5 mL of aerosolized physiologic saline (0.9% sodium chloride) was given endotracheally, followed by at least one hour of observation. After obtaining consistent measurements of PVR, 8-Br-cGMP (Sigma) was then given by aerosol endotracheally (0.03–300 µg/kg) in a 5 mL volume of physiologic saline, administered over 5 minutes, and hemodynamic data were recorded at 10–15 minute intervals. When no hemodynamic response was noted following 2 hours of administration of the lowest dose of 8-Br-cGMP (0.03 µg/kg), a higher dose was administered to establish a dose response. In separate experiments, 8-bromoguanosine 5'-monophosphate (300 µg/kg, Sigma) dissolved in 5 mL of physiologic saline was similarly administered by inhalation. After a two hour observation period, 300 µg/kg of 8-Br-cGMP dissolved in 5 mL of physiologic saline was injected intravenously as a bolus and hemodynamic measurements were recorded every 10–15 minutes.

To assess whether inhaled 8-Br-cGMP may depress myocardial contractility,[11,14] experiments were performed with or without the induction of pulmonary hypertension using the same thromboxane A2 analog. Left ventricular (LV) contractile state was assessed in these animals by measuring the end-systolic pressure-volume relations (ESPVR), with conductance used as an index of ventricular volume.[15,16] A 7 F conductance catheter (10 pole, Webster Labs Inc., Baldwin Park, Calif.) was introduced into the carotid artery and the tip positioned in the left ventricular apex under fluoroscopic guidance. The abdominal inferior vena cava was exposed and venous return was impeded as needed with a snare. LV pressure was measured using a Statham strain gauge connected to the end lumen in the conductance catheter. Data were digitized (200 Hz sampling rate) on an IBM compatible computer and analyzed off-line with custom designed software. Pressure-volume loops were obtained at different preloads during brief periods of inferior vena caval occlusion, and end-systolic pressures ($P_{es}$) and volumes ($V_{es}$) identified in the standard fashion.[15] The slope ($E_{es}$) and volume axis intercept ($V_o$) were calculated using linear regression analysis of $V_{es}$ against $P_{es}$: $P_{es} = E_{es}(V_{es} - V_o)$ Inhaled 8-Br-cGMP (30 µg/kg) was administered as described above and ESPVR measurements were taken every 15 minutes for 2 hours. To gauge the effect of a known negative inotrope, 17 an intravenous bolus of esmolol (1 mg/kg) was given after the 2 hour period, and the same measurements were obtained. CVP, PCWP, MAP, MPAP, CO, and arterial and mixed venous blood gases were recorded. Pulmonary vascular resistance (PVR, dynes sec/$cm^5$) and systemic vascular resistance (SVR, dynes sec/$cm^5$) were calculated as follows: PVR=80 (MPAP–PCWP)/CO; SVR=80 (MAP–CVP)/CO. Pulmonary shunt fraction was determined using the following formula; $Q_s/Q_t = (CcO_2 - CaO_2)/(cCO_2 - CvO_2)$, where $Q_s$=pulmonary shunt flow, and $Q_t$=total flow across the pulmonary vascular bed; $CcO_2$=pulmonary capillary $O_2$ content, $CaO_2$=arterial $O_2$ content, and $CvO_2$=mixed venous $O_2$ content.[18] Data were analyzed using Student's t-test for paired or unpaired data, as indicated. Dose response data were analyzed by ANOVA, using the Bonferroni/Dunnet posthoc comparison of individual means to test for significant differences. Data are expressed as means±SEM, with p<0.05 considered statistically significant.

Results

Figure 14:
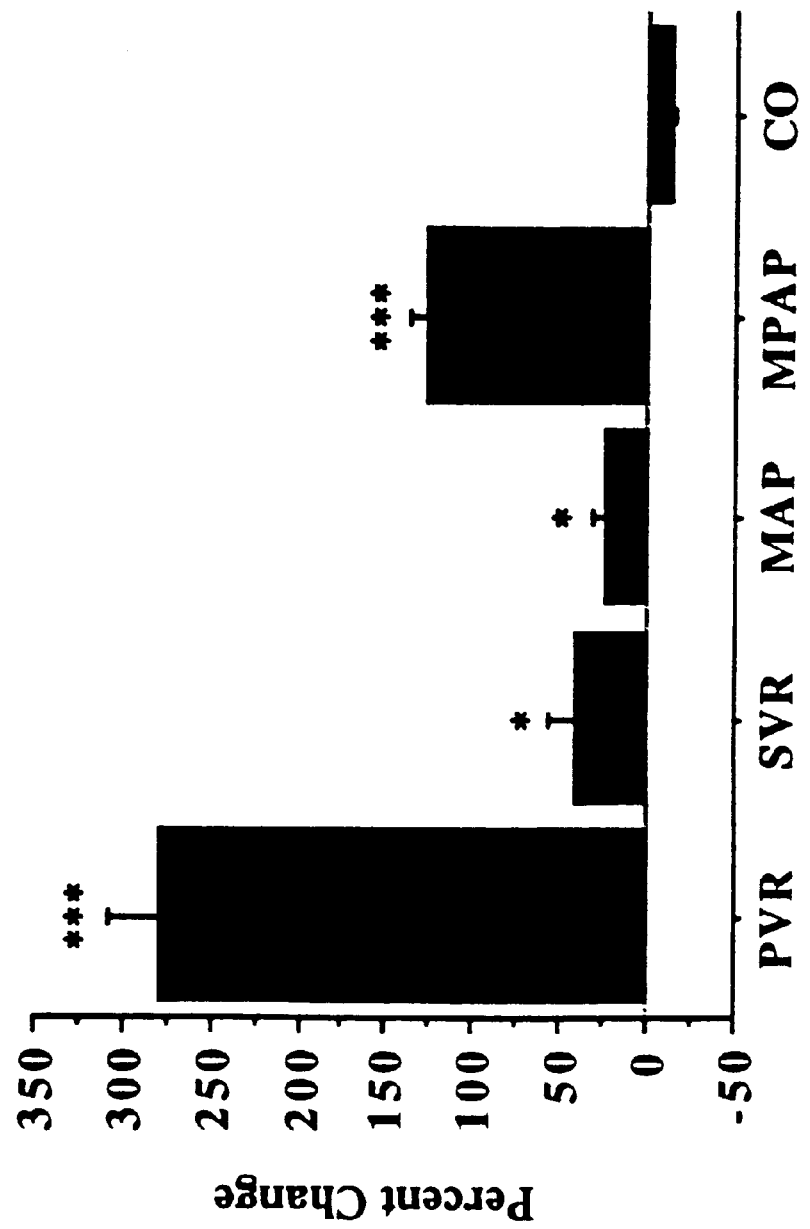
FIG. 14: Establishment of pulmonary hypertension. The thromboxane A2 analog 9,11-dideoxy-11$\alpha$,9$\alpha$-epoxymethanoprostaglandin $F_{2\alpha}$ was infused intravenously at a rate of 0.07 to 0.11 $\mu$g/kg/min to obtain a mean pulmonary arterial pressure of approximately 30 mm Hg, after which no dosage adjustments were made. Bar graphs represent the mean percent change±SEM during the thromboxane analog infusion compared with baseline values for pulmonary vascular resistance (PVR), systemic vascular resistance (SVR), mean arterial pressure (MAP), mean pulmonary arterial pressure (MPAP), and cardiac output (CO) in the animals (n=5) whose hemodynamic data is presented in Table 1.
Figure 15B:
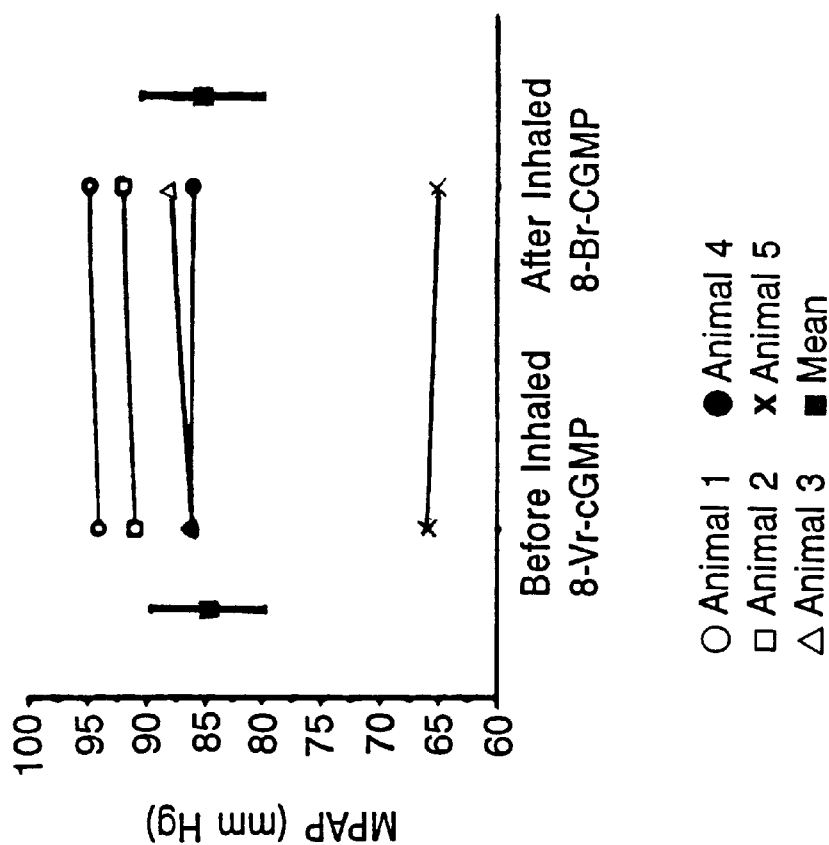
FIG. 15B: Effect of inhalationally administered 8-Br-cGMP (300 $\mu$g/kg) on hemodynamic parameters during the thromboxane analog infusion for each animal shown in Tables 1 and 2: Maximal and mean changes in MAP.
Figure 15A:
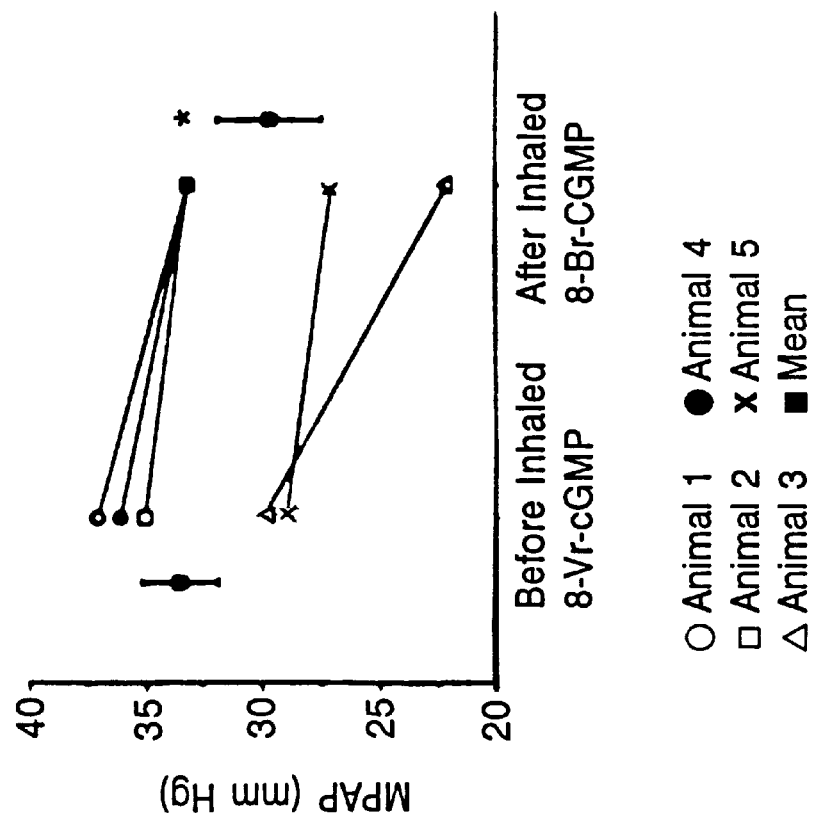
FIG. 15A: Effect of inhalationally administered 8-Br-cGMP (300 $\mu$g/kg) on hemodynamic parameters during the thromboxane analog infusion for each animal shown in Tables 1 and 2: Maximal and mean changes in MPAP ($*=p<0.05$).
Figure 15E:
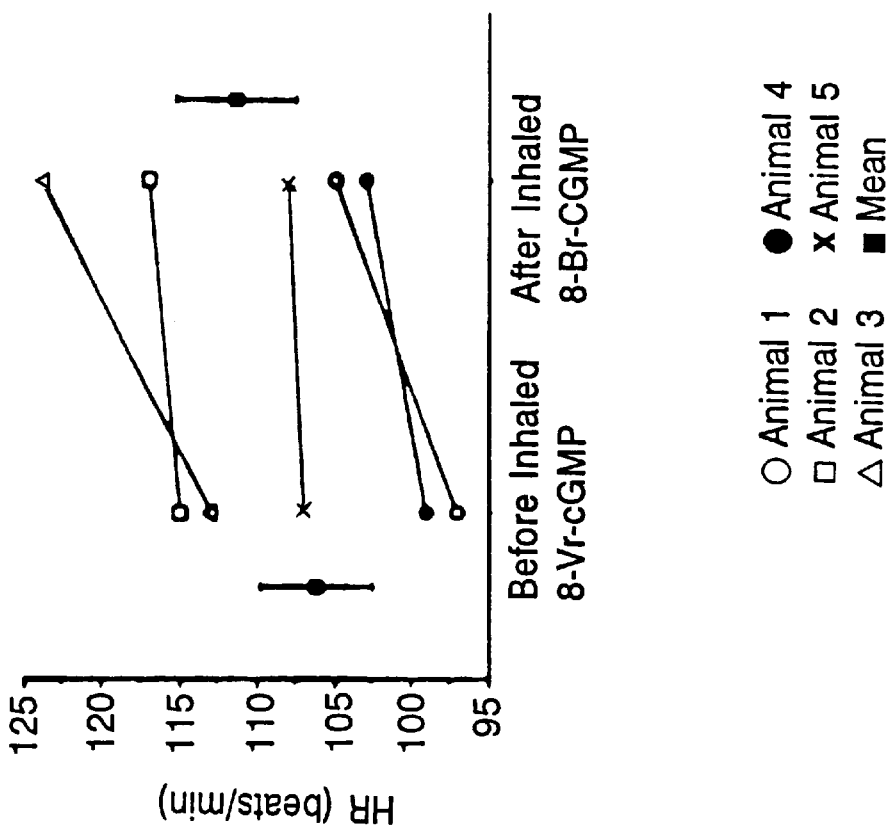
FIG. 15E: Effect of inhalationally administered 8-Br-cGMP (300 $\mu$g/kg) on hemodynamic parameters during the thromboxane analog infusion for each animal shown in Tables 1 and 2: Maximal and mean changes in CO.
Figure 15F:
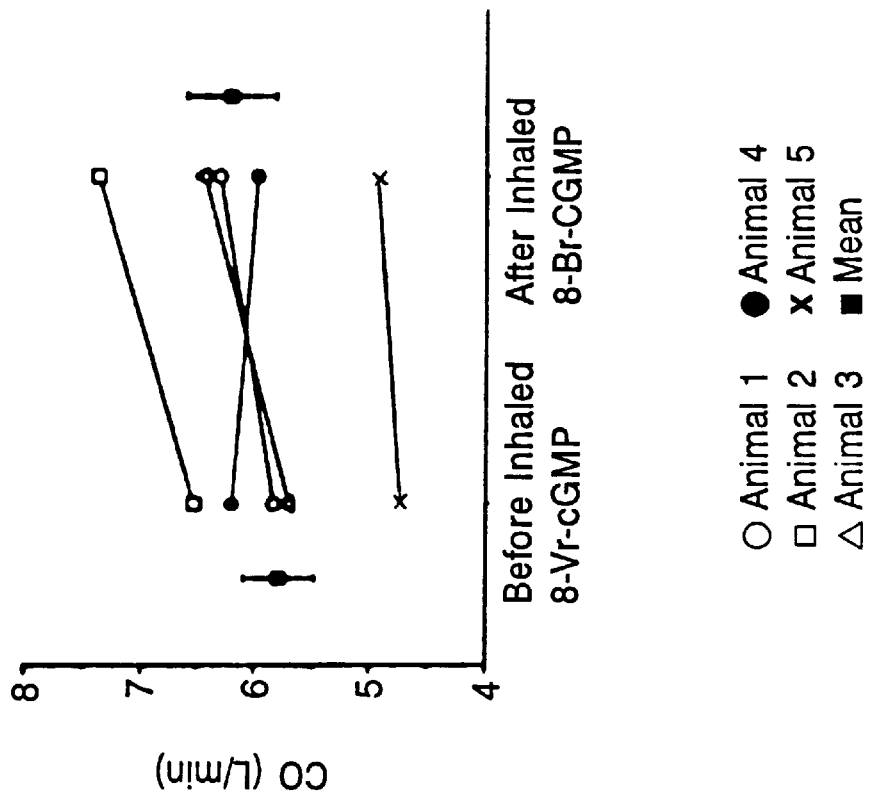
FIG. 15F: Effect of inhalationally administered 8-Br-cGMP (300 $\mu$g/kg) on hemodynamic parameters during the thromboxane analog infusion for each animal shown in Tables 1 and 2: Maximal and mean changes in HR.

Pulmonary hypertension was established in a porcine model using intravenous infusion of a potent vasoconstrictor which is an analog of thromboxane $A_2$ (9,11-dideoxy-11α, 9α-epoxymethanoprostaglandin $F_{2α}$).[10] Compared with baseline, pulmonary vascular resistance and systemic vascular resistance increased following thromboxane treatment from 102±7 to 378±8 dynes.sec/$cm^5$ for PVR (p<0.0001), and from 825±67 to 1117±31 dynes.sec/$cm^5$ for SVR (p=0.032). In addition, mean pulmonary arterial pressure increased from 15±1 to 33±2 mm Hg (p<0.0001), mean arterial pressure increased from 69±5 to 85±5 mm Hg (p=0.033), and there was a trend toward decreased cardiac output (from 7±1 to 6±0.3 L/min, p=0.069; comparative data are illustrated in FIG. 14; raw data are shown in Table 1).

After pulmonary hypertension was established, inhalation of the membrane permeable cGMP analog 8-Br-cGMP[7–9] caused a significant decline in mean pulmonary arterial pressure, central venous pressure, and pulmonary vascular resistance (data for individual animals are shown in FIGS. 15A–15H). In contrast, systemic vascular resistance did not decrease significantly, and mean arterial pressure remained unchanged following inhalation of 8-Br-cGMP.

Figure 16D:
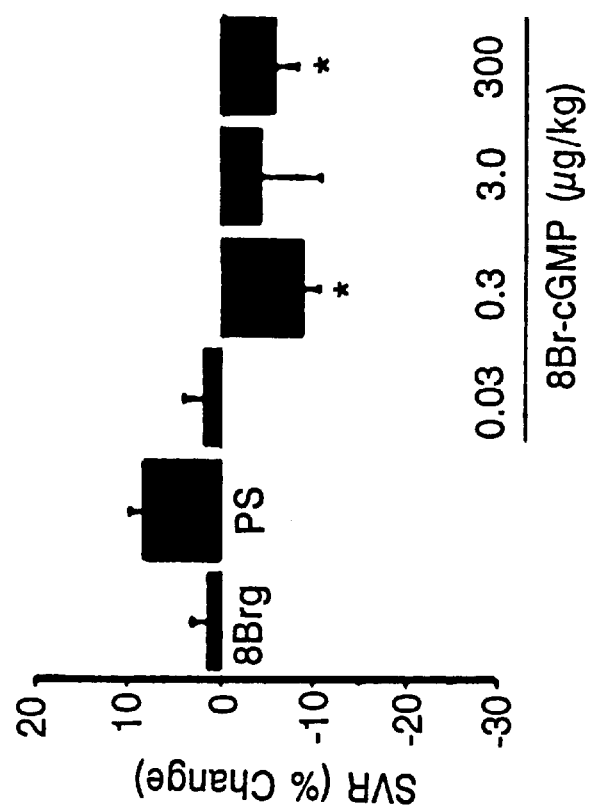
FIG. 16D: Inhalation of different doses of 8-Br-cGMP (0.03 $\mu$g/kg, n=3; 0.3 $\mu$g/kg, n=3; 3.0 $\mu$g/kg, n=3; 300 $\mu$g/kg, n=5), 8-Bromoguanosine-5'monophosphate (8Brg, n=5), or physiologic saline (PS, n=5) : Maximal changes in SVR ($*=p<0.001$ vs. PS control).
Figure 16C:
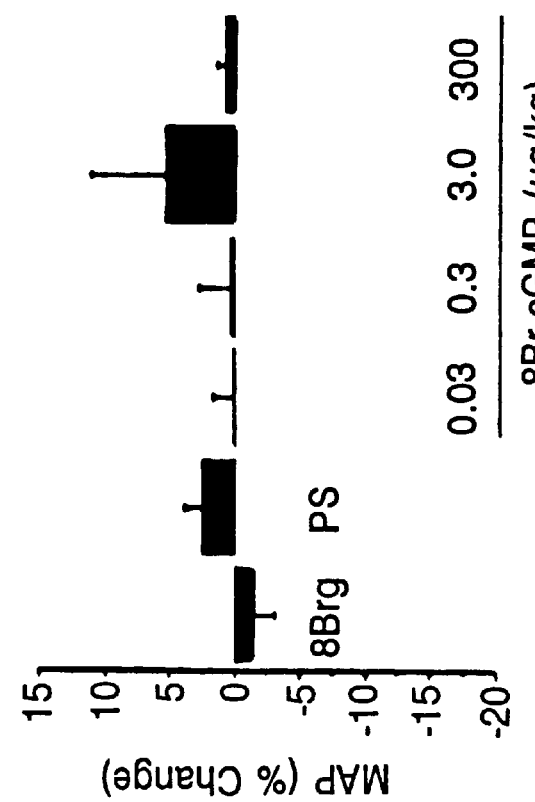
FIG. 16C: Inhalation of different doses of 8-Br-cGMP (0.03 $\mu$g/kg, n=3; 0.3 $\mu$g/kg, n=3; 3.0 $\mu$g/kg, n=3; 300 $\mu$g/kg, n=5), 8-Bromoguanosine-5'monophosphate (8Brg, n=5), or physiologic saline (PS, n=5) : Maximal changes in PVR ($**=p<0.001$ vs. PS control).
Figure 16E:
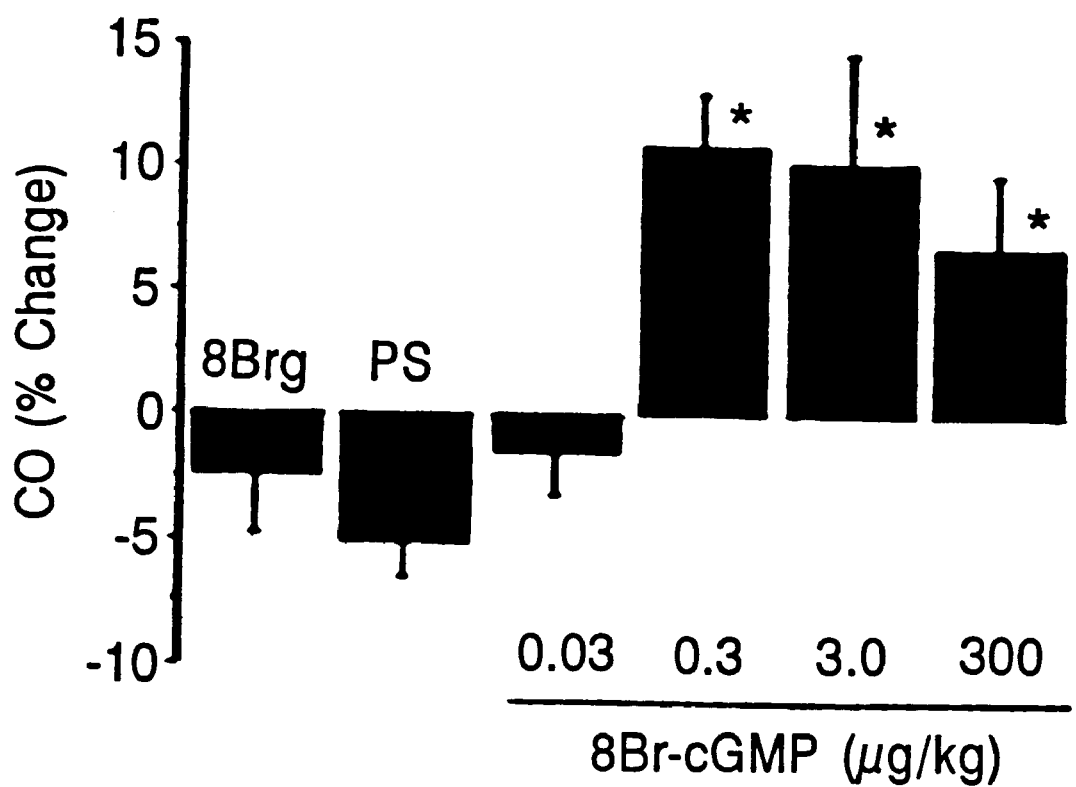
FIG. 16E: Inhalation of different doses of 8-Br-cGMP (0.03 $\mu$g/kg, n=3; 0.3 $\mu$g/kg, n=3; 3.0 $\mu$g/kg, n=3; 300 $\mu$g/kg, n=5), 8-Bromoguanosine-5'monophosphate (8Brg, n=5), or physiologic saline (PS, n=5): Maximal changes in CO ($*=p<0.003$ vs. PS control).
Figure 17A:
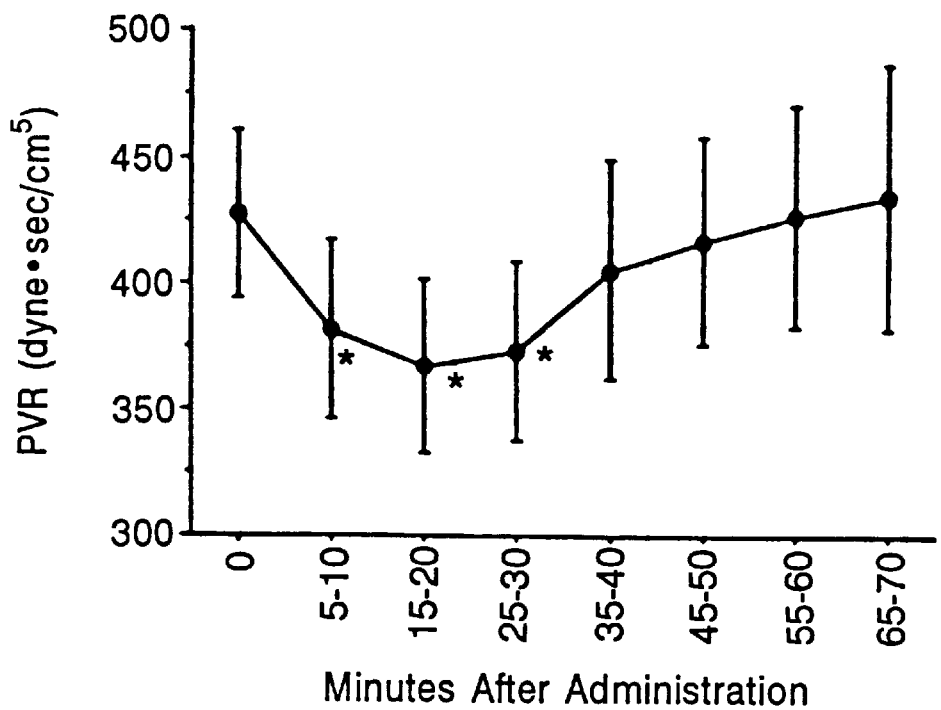
FIGS. 17A: Effect of inhaled 8-Br-cGMP on vascular resistance over time during thromboxane analog infusion. (Because doses of $\geq 3$ $\mu$g/kg similarly lowered PVR, the 3 and 300 $\mu$g/kg data were pooled to determine the time course of cGMP effect.): PVR time course ($*=p<0.05$ compared with pretreatment values).
Figure 17B:
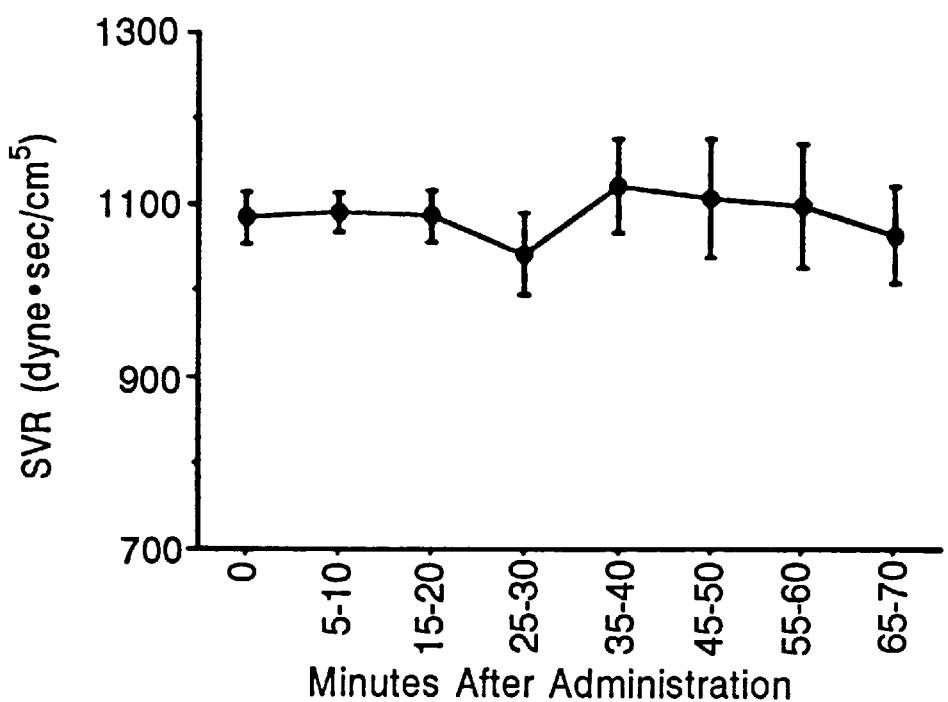
FIG. 17B: Effect of inhaled 8-Br-cGMP on vascular resistance over time during thromboxane analog infusion. (Because doses of $\geq 3$ $\mu$g/kg similarly lowered PVR, the 3 and 300 $\mu$g/kg data were pooled to determine the time course of cGMP effect.): Simultaneousl SVR time course.

In order to establish the optimal effective dose of inhaled 8-Br-cGMP, a dose-response relationship was constructed using doses ranging from 0.03 µg/kg to 300 µg/kg. The maximal decrease in pulmonary vascular resistance occurred at an inhaled dose of 3 µg/kg (−24.5±2.7% for 8-Br-cGMP vs. inhaled physiologic saline, p<0.0001), with no further decrease seen at higher doses (FIG. 16C). The lowering of pulmonary vascular resistance following inhaled 8-Br-cGMP was reflected in a significant decline in mean pulmonary arterial pressure (−12.7±2.8%), also occurring at the dose of 3 µg/kg (FIG. 16A). Mean arterial pressure was not significantly different at any given dose (FIG. 16B). In addition to its beneficial effects on pulmonary vascular resistance and mean pulmonary arterial pressure, cardiac output was significantly increased following inhalation of doses ≥0.3 µg/kg (FIG. 16E). Diminished pulmonary vascular resistance was first evident within 10 minutes of 8-Br-cGMP administration, and this effect was maximal by 20 minutes (FIG. 17A). Thereafter, pulmonary vascular resistance steadily rose back to pretreatment values.

To exclude a role for activation of purinergic receptors in the lung,[19] inhalation of the noncyclic purine nucleotide analog 8-bromoguanosine 5'-monophosphate (8-Brg) was given by inhalation. In contrast to inhaled 8-Br-cGMP (300 µg/kg), inhaled 8-Brg (300 µg/kg) failed to lower pulmonary vascular resistance, and had no significant hemodynamic effects in comparison with inhaled physiologic saline (FIG. 16A–E).

To determine whether the pulmonary vasodilator effects of inhaled 8-Br-cGMP caused increased pulmonary shunting of venous blood, arterial and venous blood gas measurements were obtained and pulmonary shunt fractions calculated.[18] Although there was no change pulmonary shunt fraction following 8-Br-cGMP inhalation (0.123±0.021 before vs. 0.152±0.037 after, p=NS), three of four animals studied did show minimal increases. There was no difference in pulmonary shunt fraction before and after 8-Bromoguanosine 5'-monophosphate inhalation (0.127±0.018 before vs. 0.123±0.023 after, p=NS, Table 2).

TABLE 1

HEMODYNAMIC EFFECTS OF THROMBOXANE ANALOG INFUSION
(Before Infusion | During Infusion)

| | Animal | | | | |
|---|---|---|---|---|---|
| | 1 | 2 | 3 | 4 | 5 |
| Heart Rate (beats/min) | 99\|97 | 107\|115 | 112\|113 | 99\|99 | 99\|107 |
| Mean Arterial Pressure (mm Hg) | 63\|94 | 87\|91 | 68\|86 | 70\|86 | 59\|66 |
| Mean Pulmonary Arterial Pressure (mm Hg) | 15\|37 | 17\|35 | 12\|30 | 18\|36 | 13\|29 |
| Central Venous Pressure (mm Hg) | 3\|6 | 1\|3 | 1\|3 | 3\|3 | 4\|5 |
| Pulmonary Capillary Wedge Pressure (mm Hg) | 7\|8 | 7\|5 | 5\|5 | 7\|7 | 7\|6 |
| Cardiac Output (L/Min) | 7.7\|5.8 | 7.0\|6.5 | 6.1\|5.7 | 7.4\|6.2 | 4.8\|4.7 |
| Pulmonary Vascular Resistance (dyne sec/$cm^5$) | 83\|397 | 115\|368 | 92\|351 | 119\|385 | 99\|389 |
| Systemic Vascular Resistance (dyne sec/$cm^5$) | 622\|1205 | 989\|1078 | 882\|1165 | 724\|1103 | 909\|1032 |

TABLE 2

EFFECT OF INHALATIONAL ADMINISTRATION ON BLOOD GAS MEASUREMENTS AND SHUNT FRACTIONS

| Animal | arterial pH | arterial $pCO_2$ (mm Hg) | arterial $pO_2$ (mm Hg) | arterial $O_2$ (% saturation) |
|---|---|---|---|---|
| 8-Bromoguanosine 5'-monophosphate treated animals (Before Administration \| After Administration of 300 μg/kg) | | | | |
| A | 7.44\|7.45 | 43\|51 | 524\|527 | 100\|100 |
| B | 7.50\|7.51 | 36\|37 | 537\|519 | 100\|100 |
| C | 7.45\|7.41 | 42\|47 | 520\|512 | 100\|100 |
| 8-Br-cGMP treated animals (Before Administration \| After Administration of 300 μg/kg) | | | | |
| 1 | 7.48\|7.47 | 40\|39 | 441\|386 | 100\|100 |
| 2 | 7.54\|7.51 | 38\|38 | 575\|497 | 100\|100 |
| 3 | 7.46\|7.47 | 39\|45 | 488\|458 | 100\|100 |
| 4* | — | — | — | — |
| 5 | 7.55\|7.54 | 34\|32 | 487\|552 | 100\|100 |

| Animal | venous pH | venous $pCO_2$ (mm Hg) | venous $pO_2$ (mm Hg) | venous $O_2$ (% saturation) | shunt fraction |
|---|---|---|---|---|---|
| 8-bromoguanosine 5'-monophosphate treated animals (before administration \| after administration of 300 μg/kg) | | | | | |
| A | 7.43\|7.43 | 52\|55 | 45\|47 | 81\|82 | 0.10\|0.08 |
| B | 7.47\|7.46 | 40\|44 | 49\|50 | 86\|88 | 0.12\|0.13 |
| C | 7.41\|7.41 | 49\|48 | 57\|58 | 89\|90 | 0.16\|0.16 |
| 8-Br-cGMP treated animals (Before Administration \| After Administration of 300 μg/kg) | | | | | |
| 1 | 7.46\|7.46 | 52\|42 | 47\|50 | 84\|87 | 0.17\|0.22 |
| 2 | 7.49\|7.47 | 45\|48 | 43\|43 | 82\|81 | 0.07\|0.11 |
| 3 | 7.44\|7.44 | 44\|51 | 50\|62 | 86\|92 | 0.14\|0.21 |
| 4* | — | — | — | — | — |
| 5 | 7.50\|7.50 | 43\|40 | 37\|38 | 76\|77 | 0.11\|0.07 |

*Blood gas analyzer unavailable for this experiment.

Figure 18:
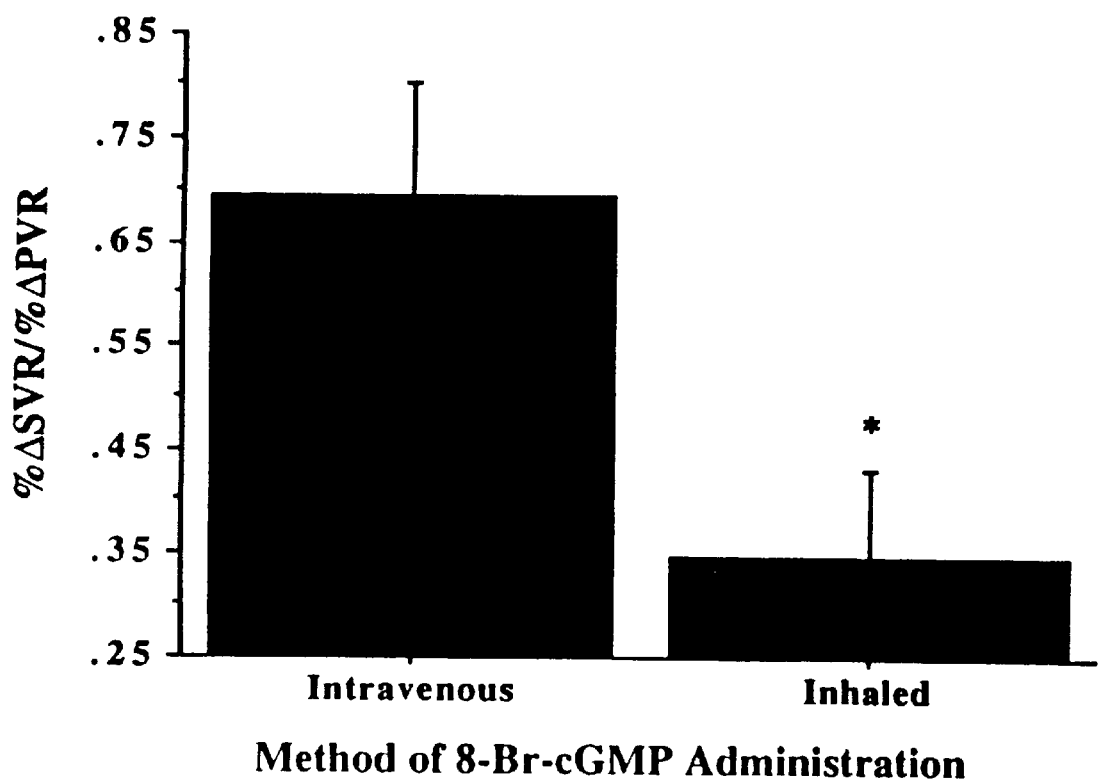
FIG. 18: The selective effect of targeted delivery of 8-Br-cGMP. 8-Br-cGMP (300 μg/kg) was dissolved in 5 mL of physiologic saline and administered by inhalation (n=5, data derived from that shown in FIG. 15), or by intravenous injection (n=4). *=p<0.05.

To investigate whether the mode of delivery was responsible for the pulmonary selectivity, identical doses of 8-Br-cGMP (300 μg/kg) were given by intravenous and inhaled routes. The change in systemic vascular resistance relative to pulmonary vascular resistance was significantly greater when the compound was given intravenously (FIG. 18). This data illustrates that intravenous delivery of 8-Br-cGMP lowers systemic vascular resistance to a greater degree than inhalational delivery, and that the inhaled route is responsible for the selective reduction of pulmonary vascular resistance.

Figure 19A:
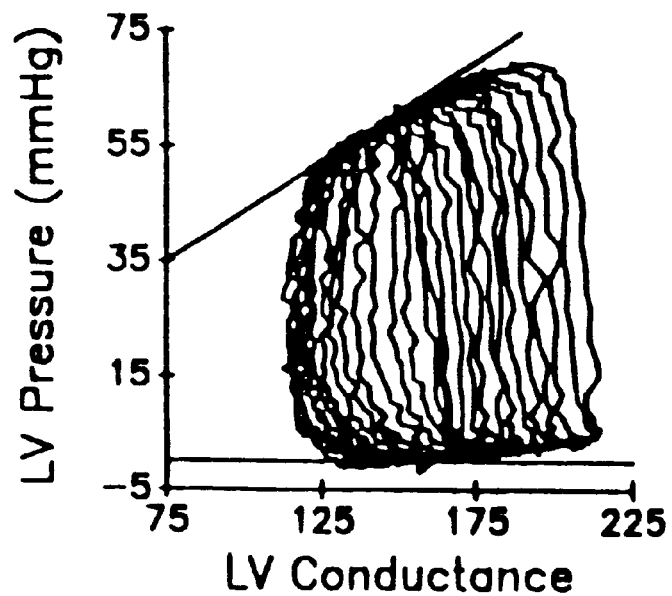
FIG. 19A: LV contractile function assessed using pressure volume loops at various preloads. Conductance reflects ventricular volume: Pressure volume loops in the untreated animal. Systolic function is described by the tangent to the pressure volume curves. This line is used as reference in the subsequent panels.
Figure 19B:
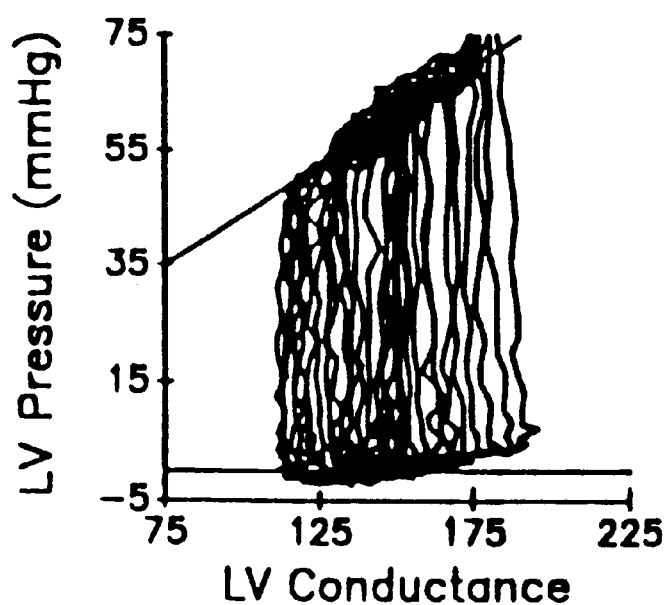
FIG. 19B: Pressure volume loops 30 min after inhalation of 8-Br-cGMP (30 μg/kg) in 5 mL of physiologic saline delivered as a mist. There is no decline in ventricular contractility.

Because 8-Br-cGMP has been reported to depress myocardial contractility[14], the effect of inhaled 8-Br-cGMP on cardiac contractility was investigated (n=3) using left ventricular conductance as an index of ventricular volume, with simultaneous measurement of intraventricular pressure. The end systolic pressure-volume relationship (ESPVR), a load-independent measure of cardiac contractility,[15,16] was determined by varying preload by controlling blood return via the inferior vena cava. In control pigs not treated with thromboxane, ESPVR was calculated before treatment (FIG. 19A) and remained unchanged after inhalation of an effective pulmonary vasodilator dose of 8-Br-cGMP (30 μg/kg, FIG. 19B). Similarly, there was no change in ESPVR following inhaled 8-Br-cGMP after establishment of pulmonary hypertension by infusion of the thromboxane $A_2$ analog (data not shown). This is in contrast to the depression of myocardial contractility observed following intravenous administration of a known negative inotrope[17] (esmolol, 1 mg/kg; FIG. 19C).

Discussion

Both primary and secondary pulmonary hypertension are associated with high morbidity and mortality. Although many therapeutic agents have been tried to lower the elevated pulmonary vascular resistance associated with these conditions, no agent has been found which is both simple to administer and consistently effective.[1,20–22] The efficacy of most agents is limited by nonselective vasodilation, whereby systemic vascular resistance is lowered to a similar or greater degree than pulmonary vascular resistance, occasionally causing a precipitous drop in blood pressure resulting in patient death.[1,21–23] A drug is considered to be clinically effective in pulmonary hypertension if it can lower pulmonary vascular resistance more than it lowers systemic vascular resistance, i.e., is relatively selective for the pulmonary vasculature.[1] Since the major clinical impact of chronic pulmonary hypertension stems from flow limitation, a goal of drug therapy is reduction of pulmonary arterial pressures and calculated pulmonary vascular resistance, with normalization of cardiac output.[22]

Inhaled nitric oxide has been shown to provide selective pulmonary vasodilation in pulmonary hypertension.[2,3] Rationale for the use of nitric oxide to treat pulmonary hypertension is based upon its ability to stimulate soluble guanylate cyclase found in smooth muscle cells throughout the vasculature, leading to an increase in intracellular cGMP and subsequent vasodilation.[24] Because nitric oxide binds rapidly to and is inactivated by hemoglobin,[25] it preferentially dilates the pulmonary vascular bed when administered by inhalation. Recent clinical studies in ARDS demonstrate that this therapy is likely to benefit patients during continuous administration.[6] However, there are practical and theoretical concerns regarding NO administration: as a gas, special delivery equipment is required; its effects are dependent on continuous administration;[3,6] its free radical structure renders it highly reactive, producing toxic metabolites such as peroxynitrite;[4,5] and it is possibly carcinogenic (associated with a positive Ames test for mutagenicity).[4]

To overcome these limitations, it was hypothesized that administration of a nonhydrolyzable, membrane permeable analog of cGMP, 8-Br-cGMP,[7–9] might have beneficial pulmonary vasodilating effects similar to NO. In isolated lung models, 8-Br-cGMP administered intravenously effectively reduced hypoxia-induced pulmonary vasoconstriction.[25] Although others have given 8-Br-cGMP intravenously,[26] this method of administration should not cause selective dilation of the pulmonary vasculature because cGMP is a ubiquitous messenger, occurring in many tissues.[7–9] It was hypothesized that inhalation of aerosolized 8-Br-cGMP would target pulmonary vascular smooth muscle, thereby selectively reducing pulmonary vascular resistance.

To test this hypothesis, a model of acute pulmonary hypertension was established using the thromboxane $A_2$ analog, 9,11-dideoxy-11α,9α-epoxymethanoprostaglandin $F_{2\alpha}$,[10] given by continuous infusion to induce pulmonary hypertension. This model may be relevant to clinical pulmonary hypertension because thromboxane is thought to play a role in diseases as varied as scleroderma, systemic lupus erythematosus, cirrhosis of the liver, and pulmonary emboli.[27–35] Others have shown that endothelium-derived relaxing factor (nitric oxide) has a significant role in blunting the pulmonary response to vasoconstrictors such as thromboxane,[10] making this model suitable to test the effects of a cGMP analog. In addition, this model was well-suited to assess pharmacologic intervention because of the stability of hemodynamic variables achieved during constant infusion of this compound.

These studies demonstrated that inhalation of aerosolized 8-Br-cGMP causes a significant dose-dependent decline in mean pulmonary arterial pressure and pulmonary vascular resistance. These changes were accompanied by an increase in cardiac output. This, in addition to the significant decrease in central venous pressure, are evidence that 8-Br-cGMP inhalation resulted in unloading of the right ventricle, a goal of pulmonary vasodilator therapy.[22] When identical doses of 8-Br-cGMP are given by either inhalational or intravenous administration, only the inhaled route selectively decreased pulmonary vascular resistance compared to systemic vascular resistance. This may be due to the fact that inhalational administration targets the pulmonary vasculature for delivery of the compound, and may serve to minimize effects elsewhere in the body. Selective pulmonary vasodilation after 8-Br-cGMP inhalation is not limited to the thromboxane analog model, however. Preliminary studies using a porcine model of hypoxia-induced pulmonary hypertension also demonstrated a greater decrease in pulmonary vascular resistance compared to systemic vascular resistance after 8-Br-cGMP inhalation (data not shown).

One theoretical benefit of inhaled vasodilators such as nitric oxide or 8-Br-cGMP is preferential vasodilation in areas of the lung where delivery is greatest, i.e., the ventilated portions of the lung. In these experiments, changes in pulmonary shunt fraction were measured to assess this, since dilation of unventilated portions of lung vasculature resulting from 8-Br-cGMP inhalation could increase pulmonary shunting of venous blood, thereby increasing shunt fraction as an undesirable side effect of global pulmonary vasodilation. Inhaled 8-Br-cGMP had minimal effect on shunt fraction, suggesting that 8-Br-cGMP given by inhalation has little adverse effect on ventilation-perfusion matching.

To understand the mechanism whereby 8-Br-cGMP acts as a pulmonary vasodilator, 8-bromoguanosine 5'-monophosphate was administered to exclude a role for purinergic receptor activation at pharmacologic doses. These receptors are widely distributed in the pulmonary vasculature and are known to effect smooth muscle tone.[19] This noncyclic compound had no effect in decreasing pulmonary vascular resistance when given at an inhaled dose (300 µg/kg) at which 8-Br-cGMP demonstrates a clear-cut decline in pulmonary vascular resistance. This suggests that the ability of 8-Br-cGMP to reduce pulmonary vascular resistance is related to its actions as a second messenger cyclic nucleotide, rather than due to nonspecific purinergic receptor activation.

It has been suggested that stimulation of the NO pathway may result in depression of myocardial contractility,[11-14] which would be of clinical concern in patients with compromised ventricular function. Depression of myocardial contractility has been ascribed to nitric oxide production,[11-13] and 8-Br-cGMP itself has been shown to exert a moderate negative inotropic effect on isolated ferret cardiac muscle,[14] so it was important to measure the effect of inhaled 8-Br-cGMP on load-independent measures of myocardial contractility. Because load-independent measures of right ventricular performance are difficult to obtain due to the geometry of the right ventricle,[36] in these studies pressure-volume loops were used to construct load-independent measures of left ventricular function following inhalation of 8-Br-cGMP. Under both normotensive and thromboxane analog induced hypertensive conditions, inhalation of 8-Br-cGMP at an effective pulmonary vasodilating dose had no effect on left ventricular ESPVR, suggesting no adverse effect on myocardial contractility.

In conclusion, inhalation of 8-Br-cGMP causes selective pulmonary vasodilation in a porcine model of pulmonary hypertension, an effect which is likely mediated by its actions as a second messenger cyclic nucleotide. The combination of an agent which stimulates the NO/cGMP pathway with a directed method of delivery (such as inhalation) suggests a broad range of pharmacologic possibilities for the treatment of pulmonary hypertension.

REFERENCES FOR SECOND SERIES OF EXPERIMENTS

1. Packer, M. Vasodilator therapy for primary pulmonary hypertension. *Ann. of Int. Med.* 103(2):258–270, 1985.

2. Pepke-Zaba, J., T. W. Higenbottam, A. T. Dinh-Xuan, D. Stone, and J. Wallwork. Inhaled nitric oxide as a cause of selective pulmonary vasodilatation in pulmonary hypertension. *Lancet.* 338(8776):1173–1174, 1991.

3. Frostell, C., M. Fratacci, J. Wain, R. Jones, and W. Zapol. Inhaled nitric oxide: a selective pulmonary vasodilator reversing hypoxic pulmonary vasoconstriction. *Circ.* 83(6): 2038–2047, 1991.

4. Arroyo, P. L., V. Hatch-Pigott, H. F. Mower, and R. V. Cooney. Mutagenicity of nitric oxide and its inhibition by antioxidants. *Mutation Research.* 281:193–202, 1992.

5. Beckman, J. S., T. W. Beckman, J. Chen, P. A. Marshall, and B. A. Freeman. Apparent hydroxyl radical production by peroxynitrite: Implications for endothelial injury from nitric oxide and superoxide. *Proc. Natl. Acad. Sci. USA.* 87:1620–1624, 1990.

6. Rossaint, R., K. Falke, F. Lopez, K. Slama, U. Pison, and W. Zapol. Inhaled nitric oxide for the adult respiratory distress syndrome. *N. Engl. J. Med.* 328(6):399–405, 1993.

7. Lincoln, T. M., and T. L. Cornwell. Intracellular cyclic GMP receptor proteins. *FASEB J.* 7:328–338, 1993.

8. Murad, F. Cyclic guanosine monophosphate as a mediator of vasodilation. *J. Clin. Invest.* 78:1–5, 1986.

9. Kuo, J. F. Molecular and physiopathologic aspects of mammalian cyclic GMP-dependent protein kinase. *Ann. Rev. Pharmacol. Toxicol.* 18:341–355, 1978.

10. Fineman, J., R. Chang, and S. Soifer. EDRF inhibition augments pulmonary hypertension in intact newborn lambs. *Am. J. Physiol.* 262(31):H1365–H1371, 1992.

11. Balligand, J-L., D. Ungureanu, R. A. Kelly, L. Kobzik, D. Pimental, T. Michel, and T. W. Smith Abnormal contractile function due to induction of nitric oxide synthesis in rat cardiac myocytes follows exposure to activated macrophage-conditioned medium. *J. Clin. Invest.* 9:2314–2319, 1993.

12. Brady, A. J. B., P. A. Poole-Wilson, S. E. Harding, and J. B. Warren. Nitric oxide within cardiac myocytes reduces their contractility in endotoxemia. *Am. J. Physiol.* 263:H1963–H1966, 1992.

13. Finkel, M. S., C. V. Oddis, T. D. Jacob, S. C. Watkins, B. G. Hattler, and R. ., Simmons. Negative inotropic effects of cytokines on the heart mediated by nitric oxide. *Science.* 257(5068) :387–389, 1992.

14. Shah, A. M., M. J. Lewis, and A. H. Henderson. Effects of 8-Bromo-cyclic GMP on contraction and on inotropic response of ferret cardiac muscle. *J. Mol. Cell Cardiol.* 23:55–64, 1991.

15. Baan, J., E. T. van der Velde, H. G. DeBruin, G. J. Smeenk, J. Koops, A. D. Van Dijk, D. Temmerman, J. Senden, and B. Buis. Continuous measurement of left ventricular volume in animals and humans by conductance catheter. *Circ.* 70:812–823, 1984.

16. Sagawa, K. The ventricular pressure-volume diagram revisited. *Circ. Res.* 43:677–687, 1978.

17. Tuman, K. J., R. J. McCarthy, C. A. Wong, A. M. Labarge, B. D. Spiess, and A. D. Ivankovich. Comparative effects of esmolol and verapamil in a model of supraventricular tachydysrhythmia. *Anesthesiology.* 73(3):467–473, 1990.

18. Stoelting, R. K., and S. F. Dierdorf; Anesthesia and Co-Existing Disease, 3rd Edition; New York; Churchhill Livingstone; 1993, p 177.

19. Dubyak, G. R. Signal transduction by $P_2$-purineregic receptors for extracellular ATP. *Am. J. Respir. Cell Mol. Biol.* 4:295–300, 1991.

20. Priebe, H-J. Efficacy of vasodilator therapy in a canine model of acute pulmonary hypertension. *Am. J. Physiol.* 255(5, pt. 2):H1232–H1239, 1988.

21. Weir, E. K., L. J. Rubin, S. Mm Ayers, E. H. Bergofsky, B. H. Brundage, K. M. Detre, C. G. Elliott, A. P. Fishman, R. M. Goldring, B. M. Groves, J. T. Kernis, S. K. Koerner, P. S. Levy, G. G. Pietra, L. M. Reid, S. Rich, C. E. Vriem, G. W. Williams, and M. Wu. The acute administration of vasodilators in primary pulmonary hypertension. Experience from the National Institutes of Health registry on primary pulmonary hypertension. *Am. Rev. Respir. Dis.* 140(6): 1623–1630, 1989.

22. Rich, S. Should patients with pulmonary hypertension and increased pulmonary resistance be treated with vasodilators? *Cardiovasc. Clin.* 21(1) :265–274, 1990.

23. Partanen, J., M. Nieminen, and K. Luomanmaki. Death in a patient with primary pulmonary hypertension after 20 mg. of Nifedipine (letter). *N. Engl. J. Med.* 329(11) :812–813, 1993.

24. Ignarro, L. Biosynthesis and metabolism of endothelium-derived nitric oxide. *Annu. Rev. Pharmacol. Toxicol.* 30:535–560, 1990.

25. Archer, S., K. Rist, D. Nelson, E. DeMaster, N. Cowan, and E. Weir. Comparison of the hemodynamic effects of nitric oxide and endothelium-dependent vasodilators in intact lungs. *J. Appl. Physiol.* 68(2):735–747, 1990.

26. Elsner, D., E. Kromer, and G. Riegger. Hemodynamic, renal, and hormonal effects of 8-Br-cyclic GMP in conscious dogs with and without congestive heart failure. *Journal of Cardiovascular Pharmacology.* 14:241–247, 1989.

27. Zamora, C. A., D. A. Baron, and J. E. Heffner. Thromboxane contributes to pulmonary hypertension in ischemia-reperfusion lung injury. *J. Appl. Physiol.* 74(1): 224–229, 1993.

28. Christman, B. W., C. D. McPhereson, J. H. Newman, G. A. King, G. R. Bernard, B. M. Groves, J. E. Loyd. An imbalance between the excretion of thromboxane and prostacyclin metabolites in pulmonary hypertension. *N. Engl. J. Med.* 327(2):70–75, 1992.

29. Ostenden, J., R. Hede, Y. Myreng, T. Ege, and E. Holtz. Intravenous injection of Albunex microspheres causes thromboxane-mediated pulmonary hypertension in pigs, but not in monkeys or rabbits. *Acta Physiol. Scand.* 144(3):307–315, 1992.

30. Byrick, R. J., J. B. Mullen, P. Y. Wong, J. C. Kay, D. Wigglesworth, and R. J. Doran. Prostanoid production and pulmonary hypertension after fat embolism are not modified by methylprednisolone. *Can. J. Anaesth.* 385(5):660–667, 1991.

31. Nuttal, G. A., M. J. Murray, and E. J. W. Bowie. Protamine-heparin-induced pulmonary hypertension in pigs: effects of treatment with a thromboxane receptor antagonist on hemodynamics and coagulation. *Anesthesiology.* 74(1): 138–145, 1991.

32. Badesch, D. B., E. C. Orton, L. M. Zapp, J. Y. Westcott, J. Hester, N. F. Voelkel, and K. R. Stenmark. Decreased arterial wall prostaglandin production in neonatal calves with severe chronic pulmonary hypertension. *Am. J. Respir. Cell. Mol. Biol.* 1(6):489–498, 1989.

33. Rostagno, C., G. F. Gensini, S. Boncinelli, M. Marsili, S. Castellani, P. Lorenzi, V. Merciai, M. Linden, G. L. Chelucci, and F. Cresci. The prominent role of thromboxane A2 formation on early pulmonary hypertension induced by oleic acid administration in sheep. *Thromb. Res.* 58(1): 35–45, 1990.

34. Pinheiro, J. M., B. R. Pitt, and C. N. Gillis. Roles of platelet-activating factor and thromboxane in group B streptococcus-induced pulmonary hypertension in piglets. *Pediatr. Res.* 26(5):420–424, 1989.

35. Seeger, W., H. Walter, N. Suttorp, M. Muhly, and S. Bhakdi. Thromboxane-mediated hypertension and vascular leakage evoked by low doses of *E. coli* hemolysin in rabbit lungs. *J. Clin. Invest.* 84(1):220–227, 1989.

36. Woodard, J. C., C. D. Bertram, and B. S. Gow. Right ventricular volumetry by catheter measurement of conductance. *PACE* 10 (1) :862–870, 1987.

What is claimed is:

1. A method of selectively decreasing pulmonary vascular resistance in a subject having a pulmonary condition selected from the group consisting of primary pulmonary hypertension, chronic obstructive pulmonary disease, adult respiratory distress syndrome, congenital heart disease, cystic fibrosis, sarcoidosis, cor pulmonale, pulmonary embolism, bronchiectasis, emphysema, Pickwickian syndrome, sleep apnea, congestive heart failure, and valvular heart disease which comprises administering endotracheally or endobronchially to a subject an effective amount of a drug selected from the group consisting of cyclic nucleotides, phosphodiesterase inhibitors, nitric oxide precursors in an aerosol form, nitric oxide donors in an aerosol form, and nitric oxide analogs in an aerosol form, thereby selectively decreasing pulmonary vascular resistance.

2. The method of claim 1 wherein the pulmonary vascular resistance is decreased by at least about twenty-four percent.

3. The method of claim 1 wherein the pulmonary vascular resistance is decreased by up to about sixty-four percent.

4. The method of claim 3 wherein the pulmonary vascular resistance is decreased between about twenty-four percent and about sixty-four percent.

5. The method of claim 1 wherein the pulmonary vascular resistance is decreased for over ninety minutes.

6. The method of claim 1 wherein the ratio of the percent change in systemic vascular resistance to the percent change in the pulmonary vascular resistance is about 0.5 or less.

7. The method of claim 6 wherein the ratio of the percent change in systemic vascular resistance to the percent change in the pulmonary vascular resistance is about 0.3 or less.

8. The method of claim 7 wherein the ratio of the percent change in systemic vascular resistance to the percent change in the pulmonary vascular resistance is about 0.04 or less.

9. A method for selectively counteracting the effects of a vasoconstrictor administered to a subject comprising the method of claim 1.

10. The method of claim 9 wherein the vasoconstrictor is thromboxane $A_2$.

11. The method of claim 9 wherein the vasoconstrictor is thromboxane $A_2$ analog U-46619.

12. A method for treating pulmonary hypertension comprising the method of claim 1.

13. A method for treating a pulmonary condition comprising the method of claim 1.

14. The method of claim 13 wherein the pulmonary condition is selected from the group consisting of primary pulmonary hypertension, chronic obstructive pulmonary disease, adult respiratory distress syndrome, congenital heart disease, cystic fibrosis, sarcoidosis, cor pulmonale, pulmonary embolism, bronchiectasis, emphysema, Pickwickian syndrome, sleep apnea, congestive heart failure, and valvular heart disease.

15. The method of claim 1 wherein the subject is a mammal.

16. The method of claim 15 wherein the mammal is a pig.

17. The method of claim 15 wherein the mammal is a human.

18. The method of claim 1 wherein the administering comprises injecting a liquid containing the drug via the trachea or a bronchus.

19. The method of claim 1 wherein the administering comprises inhaling the drug in an aerosol form.

20. The method of claim 19 wherein the aerosol is generated by a nebulizer.

21. The method of claim 19 wherein the aerosolized drug is administered as an aqueous solution.

22. The method of claim 19 wherein the aerosolized drug is administered as a micronized powder.

23. The method of claim 1 wherein the drug is a cyclic nucleotide and is membrane permeant.

24. The method of claim 1 wherein the drug is a cyclic nucleotide and is an agonist of protein kinase A.

25. The method of claim 1 wherein the drug is a cyclic nucleotide and is an agonist of protein kinase G.

26. The method of claim 1 wherein the drug is a cyclic nucleotide and increases cellular cAMP.

27. The method of claim 1 wherein the drug is a cyclic nucleotide and increases cellular cGMP.

28. The method of claim 1 wherein the drug is a cyclic nucleotide and is resistant to degradation by an enzyme.

29. The method of claim 28 wherein the enzyme is phosphodiesterase.

30. The method of claim 1 wherein the cyclic nucleotide is a cGMP analog or a cAMP analog.

31. The method of claim 30 wherein the cGMP analog is 8-bromo-3',5'-cyclic guanosine monophosphate.

32. The method of claim 30 wherein the cGMP analog is 8-PCPT-cGMP.

33. The method of claim 30 wherein the cGMP analog is Sp-8-Br-cGMPS.

34. The method of claim 26 wherein the cyclic nucleotide is a cAMP analog.

35. The method of claim 34 wherein the cAMP analog is dibutyryl-3',5'-cyclic adenosine monophosphate.

36. The method of claim 34 wherein the cAMP analog is 8-bromo-3',5'-cyclic adenosine monophosphate.

37. The method of claim 34 wherein the cAMP analog is Sp-CAMPS.

38. The method of claim 1 wherein the effective amount of the drug is at least about 0.03 micrograms per kilogram of body weight.

39. The method of claim 38 wherein the effective amount is between about 2 micrograms per kilogram of body weight to about 20 micrograms per kilogram of body weight.

40. The method of claim 1 further comprising administering a permeabilizing solvent.

41. The method of claim 40 wherein the solvent is dimethylsulfoxide.

42. The method of claim 1 wherein the phosphodiesterase inhibitor is isobutylmethylxanthine.

43. The method of claim 1 wherein the phosphodiesterase inhibitor is 2-o-propoxyphenyl-8-azapurin-6-one.

44. The method of claim 1 wherein the drug is the nitric oxide precursor L-arginine.

45. The method of claim 1 wherein the drug is a nitric oxide donor selected from the group consisting of diethylamine NONOate and spermine NONOate.

46. The method of claim 1 wherein the drug is a nitric oxide analog or donor selected from the group consisting of nitroglycerin, nitroprusside, Sin-1, and SNAP.

47. A method of selectively decreasing pulmonary vascular resistance in a subject which comprises administering endotracheally or endobronchially to a subject an effective amount of a drug selected from the group consisting of cGMP analogs, cAMP analogs, nitric oxide precursors in an aerosol form, nitric oxide donors in an aerosol form, and nitric oxide analogs in an aerosol form, thereby selectively decreasing pulmonary vascular resistance.

* * * * *